(12) United States Patent
Lagrange et al.

(10) Patent No.: US 6,458,168 B1
(45) Date of Patent: Oct. 1, 2002

(54) HAIR DYEING METHOD USING AN ALIPHATIC CATIONIC AMINE AND COMPOUND CHOSEN FROM AN ALDEHYDE, A KETONE, A QUINONE, A DI-IMINO-ISOINDOLINE, AND A 3-AMINOISOINDOLONE DERIVATIVE

(75) Inventors: Alain Lagrange, Coupvray; Hervé Andrean, Paris, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/622,711

(22) PCT Filed: Dec. 22, 1999

(86) PCT No.: PCT/FR99/03247

§ 371 (c)(1),
(2), (4) Date: Oct. 25, 2000

(87) PCT Pub. No.: WO00/38640

PCT Pub. Date: Jul. 6, 2000

(30) Foreign Application Priority Data

Dec. 23, 1998 (FR) .............................. 98 16376

(51) Int. Cl.$^7$ .................................. A61K 7/13
(52) U.S. Cl. ................. 8/405; 8/406; 8/409; 8/410; 8/411; 8/426; 8/535; 8/607; 8/608; 8/657
(58) Field of Search ............... 8/405, 406, 409, 8/410, 411, 535, 607, 608, 657, 476, 426

(56) References Cited

U.S. PATENT DOCUMENTS

| 5,034,014 | A | * | 7/1991 | Wenke ........................ 8/408 |
| 5,198,584 | A | * | 3/1993 | Chan et al. ................. 564/289 |
| 5,261,926 | A | | 11/1993 | Lang et al. ..................... 8/406 |
| 5,616,150 | A | | 4/1997 | Moeller et al. ................ 8/405 |
| 5,743,919 | A | | 4/1998 | Moeller et al. ................ 8/409 |
| 6,001,135 | A | * | 12/1999 | Rondeau et al. .............. 8/407 |
| 6,077,320 | A | * | 6/2000 | Andreau et al. .............. 8/405 |

FOREIGN PATENT DOCUMENTS

| DE | 43 14 317 | | 11/1994 | |
| DE | 44 09 143 | | 9/1995 | |
| EP | 0 502 784 | | 9/1992 | |
| EP | 0 847 749 | | 6/1998 | |
| GB | 2 181 740 | | 4/1987 | |
| GB | 2181750 A | * | 4/1987 | ............ A61K/7/13 |

* cited by examiner

*Primary Examiner*—Yogendra N. Gupta
*Assistant Examiner*—Eisa Elhilo
(74) *Attorney, Agent, or Firm*—Finnegan, Henderson, Farabow, Garrett & Dunner, LLP

(57) ABSTRACT

The present invention relates to the use, for dyeing keratin fibers, of at least one aliphatic cationic amine and of at least one compound chosen from an aldehyde, a ketone, a quinone and a diiminoisoindoline or 3-aminoisoindolone derivative, in order to obtain, by reaction without an oxidizing agent, a coloration of the said keratin fibers. The invention also relates to dye compositions comprising these compounds and to dyeing agents for using them.

68 Claims, No Drawings

HAIR DYEING METHOD USING AN ALIPHATIC CATIONIC AMINE AND COMPOUND CHOSEN FROM AN ALDEHYDE, A KETONE, A QUINONE, bx;1A DI-IMINO-ISOINDOLINE, AND A 3-AMINOISOINDOLONE DERIVATIVE

The present invention relates to the use, for dyeing keratin fibres, of at least one aliphatic cationic amine and of at least one compound chosen front an aldehyde, a ketone, a quinone and a diiminoisoindoline or 3-aminoisoindolone derivative, to dye compositions comprising a combination of these compounds, to dyeing processes using the said compounds and to a multi-compartment device containing these compounds.

It is known practice, for the dyeing of keratin fibres, and in particular of human keratin fibres such as the hair, to use direct dyes or coloured substances which give the fibre a temporary or semi-permanent coloration, of low dyeing power, which is generally removed by washing. The ranges of shades obtained by these direct processes are generally limited. It is also known practice to use oxidation dyes (oxidation bases and couplers) which are compounds which are initially colourless or weakly coloured and which, under the action of an oxidizing agent, generate coloured compounds by a process of oxidative condensation. Compared with direct colorations, oxidative colorations are permanent, powerful and withstand external agents (light, bad weather, washings perspiration and rubbing). Nevertheless, the use of the oxidizing agent can harm the keratin fibres and makes the processes for carrying out the oxidative dyeing operations relatively complex.

The Applicant has just discovered a novel dyeing process, which does not involve a process of oxidative development of dyes, and which gives a wide range of shades.

The compounds used by the Applicant are small molecules which can penetrate into keratin easily. The Applicant has found, surprisingly, that these compounds can then condense to form chromophores or dyes, bulkier molecules which remain trapped inside the keratin.

The Applicant has thus found that the dyes obtained withstand shampooing and perspiration and are stable with respect to light, bad weather and chemical agents. These colorations withstand shampooing particularly well. The Appliicint has, in a way, discovered a novel dyeing process which has the advantages of so-called oxidation dyeing without exhibiting its drawbacks, since no oxidizing agent is used.

One subject of the present invention is thus the use, for dyeing keratin fibres, of an aliphatic cationic amine and of a compound chosen from an aldehyde, a ketone, a quinone and a diiminoisoindoline or 3-aminoisoindolone derivative.

Another subject of the invention relates to dye compositions comprising these compounds.

A subject of the present invention is also a process for dyeing keratin fibres, which consists in applying an aliphatic cationic amine and a compound chosen from an aldehyde, a ketone, a quinone and a diiminoisoindoline or 3-aminoisoindolone derivative to the fibres, either simultaneously, in the form of a mixture prepared at the time of use, or successively.

Another subject of the invention also consists of a dyeing agent for carrying out the process of the invention.

Other subjects of the invention will become apparent in the light of the description and the examples which follow.

The main subject of the present invention is thus the use, for dyeing keratin fibres, in particular human keratin fibres such as human hair, of at least one aliphatic cationic amine and of at least one compound chosen from an aldehyde, a ketone, a quinone and a diiminoisoindoline or 3-aminoisoindolone derivative, in order to obtain, by reaction without an oxidizing agent, a coloration of the said keratin fibres.

For the purposes of the invention, the expression "aliphatic cationic amine"0 means a molecule comprising at least one amine function, at least one aliphatic hydrocarbon-based chain and at least one positive group, preferably a quaternary ammonium.

The aliphatic cationic amine is chosen from the compounds of formula (I) below and the cosmetically acceptable salts thereof:

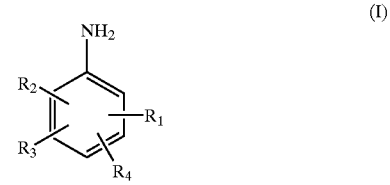

(I)

in which:

$R_1$, $R_2$, $R_3$ and $R_4$, which may be identical or different, represent a hydrogen atom; a halogen atom, an —$NH_2$ group, an —OH group; a group Z; a group —COZ; a group —COOZ; an alkylcarbonyl radical; an aminoalkylcarbonyl radical; an N-alkylaminoalkylcarbonyl radical; an N,N-dialkylaminoalkylcarbonyl radical; an aminoalkylcarbonylalkyl radical; an N-alkylaminoalkylcarbonylalkyl radical; an N,N-dialkylaminoalkylcarbonylalkyl radical; a carboxyl radical; an alkylcarboxyl radical; an alkylsulphonyl radical; an aminosulphonyl radical; an N-alkylaminosulphonyl radical; an N,N-dialkylaminosulphonyl radical; an aminosulphonylalkyl radical; an N-alkylaminosulphonylalkyl radical; an N,N-dialkylaminosulphonylalkyl radical; a carbamyl radical; an N-alkylcarbamyl radical; an N,N-dialkylcarbamyl radical; a carbamylalkyl radical; an N-alkylcarbamylalkyl radical; an N,N-dialkylcarbamylalkyl radical; an alkyl, monohydroxyalkyl, polyhydroxyalkyl, alkoxyalkyl or trifluoroalkyl radical or a cyano radical; a group $OR_i$, $SR_i$, $OR_iZ$ or $SR_iZ$ or an amino group protected with an alkylcarboxyl, trifluoroalkylcarbonyl, aminoalkylcarbonyl, carbonyl, N-alkylaminoalkylcarbonyl, N,X-dialkylaminoalkylcarbonyl, alkylcarboxyl, carbamyl, N-alkylcarbamyl, N,N-dialkylcarbamyl, alkylsulphonyl, aminosulphonyl, N-alkylaminosulphonyl, N,N-dialkylaminosulphonyl, thiocarbamyl or formyl radical, a group —COZ,or a group —COOZ;

$R_i$ denotes an alkyl, monohydroxyalkyl or polyhydroxyalkyl radical, a group Z, an alkoxyalkyl radical; an aryl radical; a benzyl radical, a carboxyalkyl radical, an alkylcarboxyalkyl radical, a cyanoalkyl radical, a carbamylalkyl radical or an N-alkylcarbamylalkyl radical; an N,N-dialkylcarbamylalkyl radical; a trifluoroalkyl radical; an aminosulphonylalkyl radical; an N-alkylaminosulphonylalkyl radical; an N,N-dialkylaminosulphonylalkyl radical; an alkylsulphinylalkyl radicalt an alkylsulphonylalkyl radical; an alkylcarbonylalkyl carbonylalkyl radical; an aminoalkyl radical; an aminoalkyl radical in which the amine is substituted with one or two radicals, which may be identical or different, chosen from alkyl, monohydroxyalkyl, polyhydroxyalkyl, alkylcarbonyl, formyl, trifluoroalkylcarbonyl, alkylcarboxyl, carbamyl, N-alkylcarbamyl, N,N-dialkylcarbamyl, thiocarbamyl and alkylsulphonyl radicals and from the groups Z, —COZ or —COOZ;

Z representing a group of formula (II) below:

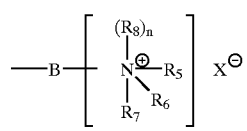

in which:

B represents a linear or branched alkyl chain, which may be interrupted by one or more hetero atoms such as oxygen, sulphur or nitrogen atoms, and which may be substituted with one or more hydroxyl or $C_1$–$C_6$ alkoxy radicals;

$R_5$, $R_6$ and $R_7$, which may be identical or different, represent an alkyl radical, a monohydroxyalkyl radical, a polyhydroxyalkyl radical, an alkoxyalkyl radical, a cyanoalkyl radical, an aryl radical, a benzyl radical, a carbamylalkyl radical, a trialkylsilanealkyl radical or an aminoalkyl radical in which the amine is protected with an alkylcarbonyl, carbamyl or alkylsulphonyl radical, two of the radicals $R_5$, $R_6$ and $R_7$ can also, form, together with the nitrogen atom to which they are attached, a 5- or 6-membered ring which, can contain one or more hetero atoms, the said ring possibly being substituted or unsubstituted, one of the radicals $R_5$, $R_6$ and $R_7$ can also represent a linker arm B' of a second radical Z, B' having the same meaning as that indicated above for the radical B;

$X^-$ represents a monovalent or divalent anion, and preferably represents a halogen atom such as chlorine, bromine, fluorine or iodine, a hydroxide, a hydrogen sulphate or an alkyl sulphate such as, for example, a methyl sulphate or an ethyl sulphate;

$R_8$ represents an alkyl, monohydroxyalkyl or polyhydroxyalkyl radical, an aryl radical; a benzyl radical; an aminoalkyl radical, an aminoalkyl radical in which the amine is protected with an alkylcarbonyl, carbamyl or alkylsulphonyl radical; a carboxyalkyl radical; a cyanoalkyl radical; a carbamylalkyl radical; a trifluoroalkyl radical; a trialkylsilanealkyl radical; a sulphonamidoalkyl radical; an alkylcarboxyalkyl radical; an alkylsulphinylalkyl radical; an alkyleulphonylalkyl radical; an alkylketoalkyl radical; an N-alkylcarbamylalkyl radical; an N-alkylsulphonamidoalkyl radical;

n is an integer equal to 0 or 1, it being understood that:
when n=0, the linker arm B is attached to the nitrogen atom bearing the radicals $R_5$ to $R_7$;
when n=1, then two of the radicals $R_5$ to $R_7$ form, together with the nitrogen atom to which they are attached, a saturated 5- or 6-membered ring which can contain one or more hetero atoms, the said ring possibly being substituted or unsubstituted, and the linker arm B is borne by a carbon atom of the said saturated ring outside of the nitrogen atom N.; and the compound (I) defined above contains at least one group Z.

Among the compounds of formula (I) which may be mentioned in particular are:

[2-(2,4-diaminophenoxy)ethyl]diethylmethylammonium chloride;

[3-(2,4-diaminophenoxy)propyl]triethylammonium chloride;

[2-(2,4-dihydroxyphenyl) -2-oxoethyl]triethylammonium chloride;

[2-(4-amino-2-hydroxyphenoxy)ethyl] diethylmethylammonium chloride;

triethyl[2-(3-hydroxy-4-methylphenylamino)-ethyl] ammonium bromide;

triethyl[2-(3-hydroxy-2,4-dimethylphenylcarbamoyloxy) ethyl]ammonium chloride;

[2-(4-chloro-5-hydroxyphenylamino)ethyl]-triethylammonium bromide;

[2-(2,4-diaminophenoxy)ethyl]diethylmethylammonium chloride;

[2-(2,4-diaminophenyl)ethyl]triethylammonium chloride;

triethyl[(3-hydroxy-4-methylphenylcarbamoyl) methylammonium chloride;

[2-[4-(dimethylamino)salicylamido]ethyl] diethylmethylammonium iodide;

ethyl(2-hydroxyethyl)dimethylammonium 4-(methylamino) salicylate bromide;

3-[(4-amino-2-hydroxybenzoyl)oxy]-N-ethyl-N,N-dimethyl-1-propylammonium iodide;

[3-(4-amino-2-hydroxybenzoyl)oxy]-N,N,N-trimethyl-1-propylammonium iodide;

triethyl(2-hydroxyethyl)ammonium 4-amino-salicylate bromide;

2-[(4-amino-2-hydroxybenzoyl)oxy]-N,N-diethyl-N-methylethylammonium iodide;

2-[(4-amino-2-hydroxybenzoyl)oxyl-N-ethyl-N,N-dimethylethylammonium iodide;

ethyl(2-hydroxyethyl)dimethylammonium 4-amino-salicylate bromide;

2-[(4-amino-2-hydroxybenzoyl)oxy]-N,N,N-trimethylethylammonium iodide;

{2-[2-aminophenylamino]ethyl}trimethylammonium monochloride monohydrate;

[2-(2-amino-5-chlorophenylamino)ethyl] trimethylammonium monochloride;

[2-(2-amino-6-chlorophenylamino)ethyl] trimethylammonium monochloride;

[2-(2-amino-4-chlorophenylamino)ethyl] trimethylammonium monochloride;

{2-[2-amino-4-chloro-5-(2hydroxyethoxy)-phenylamino] ethyl}trimethylammonium monochloride;

[2-(2-amino-5-methoxyphenylamino)ethyl] trimethylammonium monochloride;

[2- (2-amino(2-hydroxyethyl)phenylamino)ethyl] dimethylammonium monobromide;

[3- (2-aminophenylamino)propyl]diethylmethylammonium monochloride,

[2- (2-amino-4-methylphenylamino)ethyl] trimethylammonium monochloride;

[2-(2,5-diaminophenoxy)ethyl]diethylmethylammonium chloride monohydrate;

N,N-bis(trimethylammoniumpropyl)-4-aminoaniline dichloride;

[4-(4-aminophenylamino)pentyl]diethylmethylammonium chloride;

[4-(4-aminophenylamino)pentyl]diethyl (2-hydroxyethyl) ammonium chloride;

[2-(4-aminophenylamino)ethyl]diethylmethylammonium chloride;

{2[(4-aminophenyl)methylamino]ethyl}trimethylammonium chloride;
and the addition salts thereof with an acid.

The compounds (I) preferentially used are those chosen from;

[3-(4-aminophenylamino)propyl]trimethylammonium chloride;
[2-(4-aminophenylamino)propyl]trimethylammonium chloride;
[4-(4-amino-2-methylphenylamino)pentyl]diethylmethylammonium chloride;
[4-(4-amino-3-methylphenylamino)pentyl]diethylmethylammonium chloride;
N1,N4-bis[3-N-methyl-N-(4'-aminoaniline)ethyl]-1,1,4,4-tetramethyldiammonium 1,3-propane dibromide dihydrabromide monohydrate;
N1,N3-bis[3-N(4'-amionaniline)propyl]-1,1,3,3-tetramethyldiammonium 1,3-propane dibromide monohydrate;
1,3-bis{[2-(4-aminoaniline)propyl]-1,1,3,3,-tetramethyldiammoniumpropane dibromide;
1,3-bis{[4-(4-aminoaniline)pentyl]-1,1,3,3-tetramethyldiammoniumpropane dichloride;
[4-(4-aminophenylamino)pentyl](5-amino-2-hydroxybenzyl)diethylammonium monochloride;
[2-(4-aminophenylamino)propyl](5-amino-2-hydroxybenzyl)dimethylammonium monochloride;
N1, N3-bis[3-N-(2'-aminoaniline)propyl]-1,1,3,3-tetramethyldiammonium 1,3-propane dibromide;
1,3-bis{[2-(2,4-diaminophenoxy)ethyl]diethylammonium}propane dibromide;
and the addition salts thereof with an acid.

The aldehyde can correspond to formula (III) below:

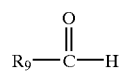

(III)

in which:

$R_9$ denotes a group of formula (III A) below:

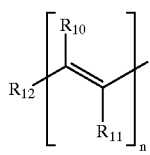

(III A)

in which:

$R_{10}$ and $R_{11}$, which may be identical or different, denote a hydrogen atom or an alkyl, mono- or polyhydroxyalkyl, alkylhydroxyalkyl, alkoxy, —$CF_3$ or —$OCF_3$ group, $R_{10}$ and $R_{11}$ can also form, together with the atoms to which they are attached, an aryl ring or a 5- or 6-membered heterocyclic ring, it being possible for the said rings to be substituted or unsubstituted;

n denotes an integer from 0 to 3, $R_{12}$ denotes the substituents denoted by $R_{10}$, a substituted or unsubstituted aryl or alkylaryl group or a substituted or unsubstituted 5- or 6-membered hetero-cyclic group, or to the cosmetically acceptable salts of these compounds.

The ketone can be chosen from the ketones of formula (Iv) or (V) below:

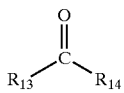

(IV)

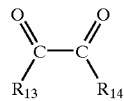

(V)

in which;

$R_{13}$ denotes the substituents denoted by $R_9$, $R_{14}$ denotes an alkyl, mono- or polyhydroxyalkyl or alkylhydroxyalkyl group, or a substituted or unsubstituted aryl, alkylaryl or 5- or 6-membered heterocyclic group, $R_{13}$ and $R_{14}$, can also form, together with the atoms to which they are attached, a 5- or 6-membered aryl ring or a heterocyclic ring comprising hetero atoms such as N or S, it, being possible for the said ring itself to be attached to a 5- or 6-Membered aryl ring or to a heterocycle comprising hetero atoms such as N or S, it being possible for the said rings to be sustituted or unsubstituted, or to the cosmetically acceptable salts of these compounds.

The quinone can correspond to formlae (VI) and (VII) below:

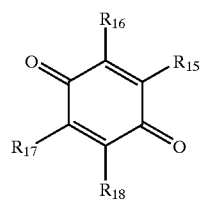

(VI)

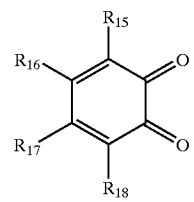

(VII)

in which:

$R_{15}$ denotes a hydrogen or halogen atom or a sulphonic or alkoxy group, $R_{16}$, $R_{17}$ and $R_{18}$, which may be identical or different, denote a hydrogen or halogen atom, a hydroxyl, alkyl, mono- or polyhydroxyalkyl, alkylhydroxyalkyl, alkylsulphonyl, carboalkyl, aminoalkyl, alkylaminoalkyl, (dihydroxy)alkylaminoalkyl or alkyl-NR'R" group (with R' and R" denoting alkyl or possibly forming, together with the nitrogen atom to which they are attached, an aryl ring or a 5- or 6-membered heterocycle), an aryl group or an amino group which can be substituted with an alkyl or a hydroxyalkyl, $R_{15}$ and $R_{16}$, $R_{16}$ and $R_{17}$ or $R_{17}$ and $R_{18}$ can form, together with the atoms to which they are attached, a substituted or unsubstituted aryl ring or 5- or 6-membered heterocycle;

or to the cosmetically acceptable salts of these compounds.

The diiminoisoindoline or 3-aminoisoindolone derivatives can be those corresponding to formula (VIII) below:

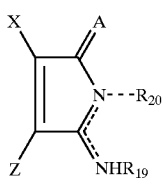

(VIII)

in which:
- $R_{19}$ and $R_{20}$, which may be identical or different, denote a hydrogen atom, an alkyl, mono- or polyhydroxyalkyl, alkylhydroxyalkyl, aminoalkyl, alkylaminoalkyl or (dihydroxy)alkylaminoalkyl group or an alkyl-NR'R" group, with R' and R" denoting alkyl or possibly forming, together with the nitrogen atom to which they are attached, an aryl ring or a 5- or 6-membered heterocycle),
- A denotes an oxygen atom or NH,
- X and Z together form a substituted or unsubstituted aryl ring or a 5- or 6-membered heterocycle;

or to the cosmetically acceptable salts of these compounds.

Among the preferred compounds of fornmla (III) which may be mentioned in particular are benzaldehyde, 2,3,4-monohydroxybenzaldehydes, 2,3,4-monomethoxybenzaldehydes, 2,3,4-monomethylbenzaldehydes, (2,3)-, (2,4)-, (2,5)-, (2,6)- and (3,5)-dihydroxybenzaldehydes, (2,3)-, (2,4)-, (2,5)-, (2,6)- and (3,5)-dimethoxybenzaldehydes, vanillin, isovanillin, syringaldehyde, ortho-, iso- and terephthalaldehyde, (2,3)-, (2,4)-, (2,5)-, (2,6)- and (3,5)-dimethylaminobenzaldehydes, 4-isopropylbenzaldehyde, 4-dimethylaminobenzaldehyde, 4-diethylaminobenzaldehyde, piperonal, (2,6)- and (3,5)-dimethyl-4-hydroxybenzaldehyde, 2,3,4-mononitrobenzaldehydes, 2-hydroxy3-methoxybenzaldehyde, 2-hydroxy-4-methoxybenzaldehyde, 2-hydroxy-5-methoxybenzaldehyde, 2-hydroxy-6-methoxybenzaldehyde, 4-methylthiobenzaldehyde, (2,3,4)-, (2,4,6)-, (3,4,5)- and (2,4,5)-trihydroxybenzaldehydes, methyl 2-, 3- and 4-formyl benzoates, 2,3,4-mono(2-hydroxyethoxy) benzaldehydes, 4-nitro-3-hydroxybenzaldehyde, 3-nitro-4-hydroxybenzaldehyde, 2-nitro-4-hydroxybenzaldehyde, 3-nitro-2-hydroxybenzaldehyde, 2,3,4-monotritluorobenzaldehydes, 2,3-dihydroxy-4-methoxybenzaldehyde, 3,4-dihydroxy-5-methoxybenzaldehyde, 3,5-dihydroxy-4-methoxybenzaldehyde, 3-methoxy-2-nitrobenzaldehyde, 4-methoxy-2-nitrobenzaldehyde, 2-methoxy-3-nitrobenzaldehyde, 4-methoxy-3 -nitrobenzaldehyde, (2,3,4)-, (2,4,6)-, (3,4,5)- and (2,4,5)-trimethoxybenzaldehydes, 5-nitro-vanillin, (2,4)- and (2,6)-dinitrobenzaldehydes, pentamethylbenzaldehyde, 4-methyloulphonylbenzaldehyde, 2,3,4-monoformylphenoxyacetic acids, 4-diethylaminosalicylaldehyde, 4-(3-dimethylaminopropoxy)benzaldehyde, 2,3-dihydrobenzo(b)furan-5-carboxaldehyde, 1-and 2-naphthaldehyde, 6- and 5-carboxaldehyde-1,4-benzodioxane, 2,4-monohydroxy-1-naphthaldehydes, 1 -monohydroxy-2-naphthaldehyde, 1-(4-formylphenyl)imidazole, 4-pyrrolidinobenzaldehyde, 2,4-monomethoxy-1-naphthaldehydes, 2,3-dimethylchroman-6 -carboxaldehyde, 2,3,6,7-tetrahydro-1H,5H-pyrido(3,2,1-IJ)quinoline-9-carbaldehyde, 4-dimethylamino-1-naphthaldehyde, 9-anthraldehyde, 3-nitro-4-pyrrolidinobenzaldehyde, 3 -nitro-4-piperidinobenzaldehyde, 3-nitro-4-morpholinobenzaldehyde, pyridine-2,3,4-monocarboxaldehydes, 2,6-pyridinodicarboxaldehyde, 5-formyl-6-methyluracil, pyridoxal, quinoline-2 ,3,4-monocarboxaldehydes, 8-hydroxyquinoline-2-carboxaldehyde, 2- and 3-furaldehydes, 2- and 3-thienylcarboxaldehydes, 2- and 3-imidazocarboxaldehydes, 2-pyrrolecarboxaldehyde, 5-nitro-2-furaldehyde, 5- (dimethylamino)--2furaldehyde, 2,5- and 2,3-thiophenedicarboxaldehydes, pyrazole-3-carbalhyde, 5-nitro-2-thiophenecarboxaldehyde, 5-nitro-3-thiophenecarboxaldehyde, indole-3-carboxaldehyde, N-methylindole-3-carboxaldehyde, 2-methylindole-3-carboxaldehyde, 4,5,6,7-monomethylindolecarboxaldehydes and 5-formyl-2-furansulphonic acid.

The ketones of formulae (IV) and (V) can be chosen from 2,3-indolinedione, 2,3-butanedione, 2,3-pentanedione, (2,3)- and (3,4)-hexanedione, 1-phenyl-1,2-propanedione, benzil, furil, 2,2'-pyridil, nitro-benzil, benzil, anisil, 3,3'-dimethoxybenzil, 4,4'-bis-(dimethylamino)benzil, camphoroquinone, cyclohexane-1,2-dione, isatin, N-methylisatin, 4,5,6,7-monomethylisatin, (4,5)-, (4,7)-, (5,7)- and (6,7)-dimethylisatin, N-ethylisatin, N-hydroxymethylisatin, 5-, 6- and 7-monomethoxyisatin, 4-, 5-, 6- and 7-monochloroisatin, 4-, 5-, 6- and 7-monobromoisatin, N-isopropylieatin, N-butylisatin, N-propylisatin, 5-nitroisatin, isatin-5-sulphonic acid, 2,4,5-trihydroxypyrimidine, alloxan, 1,3-dimethylhexahydro-2,4, 5,6-pyrimidinetetraone, ninhydrin, chinisatin, 1,3-indenedione, squaric acid, croconic acid, 3,4-dimethoxy-3-cyclobutene-1,2-dione, 3- and 4-ethoxy-3-cyclobuten-1,2-dione, 3- and 4-isopropoxy-3-cyclobutene-1,2-dione, 3,4-di-N-butoxy-3-cyclobutene-1,2-dione, rhodizonic acid, oxindole, N-methyl-2-indolinone, N-methylnitro-2-indolinone, 6-methoxyoxindole, 5,6-dimethoxyoxindole and 5- and 6- monochlorooxindole.

The preferred quinones of formulae (VI) and (VII) are, inter alia, 1,4-naphthoquinone, spinulosin, atromentin, aurentioglyocladin, 2,5-dihydroxy-6-methylbenzoquinone, 2-hydroxy-3-methyl-6-methoxybenzoquinone, 2,5-dihydroxy-3,6-diphenylbenzoquinone, 2,3-dimethyl-5-hydroxy-6-methoxybenzoquinone, 2,5-dihydroxy-6-isopropylbenzoquinone, lawsone, juglone, fafioline, naphthazarine, naphthopurpurine, lapachol, plumbagin, chloroplumbagin, droserone, shikonine, 2-hydroxy-3-methyl-1,4 -naphthoquinone, 3,5-dihydroxy-1,4-naphthoquinone, 2,5-dihydroxy-1,4-naphthoquinone, 2-methoxy-5-hydroxy-1,4-naphthoquinone, 3-methoxy-5-hydroxy-1,4-naphthoquinone, (1,4)- and (1,2)-naphthoquinone, 4,5-dimethoxy-1,2-benzoquinone, phenanthrenequinone and (1,2)-naphthoquinone-4-sulphonic acid.

The derivatives of formula (VIII) are represented in particular by 3-imino-3H-isoindolylamine, 3-imino-4-methyl-3H-isoindol-1-ylamine, 3-imino-4-tert-butyl-3H-isoindol-1-ylamine, 3-imino-7-nitro-3H-isoindol-1-ylamine, 3-amino-1-imino-1H-isoindol-4-ol, 3-imino-7-isopropoxy-3H-isoindol-1-ylamine, 3-imino-7-(2,2,2-trifluoroethoxy)-3H-isoindol-1-ylamine, 3-imino-7-ethoxy-3H-isoindol-1-ylamine, 3-imino-7-butoxy-3H-isoindol-1-ylamine, 3-amino-1-imino-1H-isoindole 4 sulphonic acid, 3-imino-7-chloro-3H-isoindol-1-ylamine, 3-imino-5-methyl-3H-isoindol-1-ylamine, 3-imino-5-ethyl-3H-isoindol-1-ylamine, 3-imino-5-tert-butyl-3H-isoindol-1-ylamine, 3-imino-5-amino-3H-isoindol-1-ylamine, N-(1-amino-3-imino-3H-isoindol-5-yl)acetamide, 3-imino-5-nitro-3H-isoindol-1-ylamine, 3-imino-5-fluoro-3H- isoindol-1-ylamine, 3-imino-5-chloro-3H-isoindol-1-ylamine, 3-imino-5-methylsulphanyl-3H-isoindol-1-ylamine, 3-imino-5-methoxy-3H-isoindol-1-ylamine, 3-imino-5-ethoxy-3H-isoindol-1-ylamine, 3-imino-5-propoxy-3H-isoindol-1-ylamine, 3-imino-5-isopropoxy-3H-isoindol-1-ylamine, 3-imino-5-butoxy-3H-isoindol-1-ylamine, 3-imino-5-isobutoxy-3H-isoindol-1-ylamine, 3-imino-5-tert-butoxy-3H-isoindol-1-ylamine, 3-imino-5-(2,2,2-trifluoromethyl)-3H-isoindol-1-ylamine, 3-imino-5-(2,2,2-trifluoroethoxy)-3H-isoindol-1-ylamine, 3-imino-5-methanesulphonyl-3H-isoindol-1-ylamine, 3-imino-5,6-dimethyl-3H-isoindol-1-ylamine, 3-imino-5,6-diethyl-3H-isoindol-1-ylamine, 3-imino-5,6-dimethoxy-3H-isoindol-1-ylamine, 3-imino-5,6-diethoxy-3H-isoindol-1-ylamine, 3-imino-5,6-dibutoxy-3H-isoindol-1-ylamine, 3-imino-5,6-bis(trifluoromethyl)-3H-isoindol-1-ylamine, 3-imino-5,6-dichloro-3H-isoindol-1-ylamine, 5,6-bis(ethoxymethyl)3-imino-3H-isoindol-1-ylamine, 3-amino-1-imino-1H-isoindole-4,7-diol, 4,7-dichloro-3-imino-3H-isoindol-1-ylamine, 4,5,7-trichloro-3-imino-N6,N6-dimethyl-3H-isoindole-1,6-diamine, 4,5,6,7-tetrachloro-3-imino-3H-isoindol-1-ylamine, 4,5,6,7-tetrafluoro-3-imino-3H-isoindol-1-ylamine, 3-butylimino-3H-isoindol-1-ylamine, 2-(3-aminoisoindol-1-ylideneamino)ethanol, 3-(3-aminoisoindol-1-ylideneamino)-3-methylpentane-1,5-diol, N-(3-aminoisoindol-1-ylidene)guanidine, 7-imino-7H-pyrrolo[3,4-b]pyrid-5-ylamine, 7-imino-7H-pyrrolo[3,4-b]pyrazin-5-ylamine, 7-imino-2,3-dimethyl-7H-pyrrolo-[3,4-b]pyrazin-5-ylamine, 7-imino-7H-[1,4]dithiino[2,3-c]pyrrol-5-ylamine, 7-imino-2,3-dimethyl-7H-[1,4]dithiino[2,3-c]pyrrol-5-ylamine, 7-imino-2,3-dihydro-7H-[1,4]dithiino[2,3-c]pyrrol-5-ylamine, 7-imino-2-methyl-2, 3-hihydro 7H [1,4]dithiino[2,3-c]pyrrol-5-ylamine 3-aminoisoindol-1-one, 3-amino-7-methylisoindol-1-one, 3-amino-7-hydroxymethylisoindol-1-one, 3-amino-7-chloroisoindol-1-one, 3-amino-4-chloroisoindol-1-one, 3-amino-1-oxo-1H-isoindole-4-sulphonic acid, 3-amino-4-nitroisoindol-1-one, 3-amino-6-nitroisoindol-1-one, 3-amino-6-methylisoindol-1-one, 3-amino-6-chloroisoindol-1-one, 3-amino-6-bromoisoindol-1-one, 3-amino-6-methylsulphanylisoindol-1-one, 3-amino-6-methoxyisoindol-1-one, 3-amino-5-chloroisoindol-1-one, 3-amino-5-fluoroisoindol-1-one, 3-amino-5-methoxyisoindol-1-one, 3-amino-5-nitroisoindol-1-one, ethyl 3-amino-1-oxo-1H-isoindole-5-carboxylate, 3-amino-5,6-dichloroisoindol-1-one, 3-amino-5,6-dibromoisoindol-1-one, 3-amino-4,7-dichloroisoindol-1-one, 3-amino-4,5,7-trichloroisoindol-1-one, 3-amino-4,5,6,7-tetrachloroisoindol-1-one, 3-amino-4,5,7-trichloro-6-methylsulphanylisoindol-1-one, 3-amino-4,5,6,7-tetrabromoisoindol-1-one, 3-amino-4,5,6,7-tetrafluoroisoindol-1-one, 3-methylaminoisoindol-1-one, 3-ethylaminoisoindol-1-one, 3-propylaminoisoindol-1-one, 3-dimethylaminoisoindol-1-one, 7-ethylaminopyrrolo[3,4-b]pyrid-5-one, 7-aminopyrrolo[3,4-b]pyrid-5-one, 3-aminopyrrolo[3,4-c]pyrid-5-one, 3-amino-6-methylpyrrolo[3,4-c]pyrid-1-one, 5-aminopyrrolo[3,4-b]pyrid-7-one, 7-aminopyrrolo[3,4-b]pyrazin-5-one, 7-amino-2-methylpyrrolo[3,4-b]pyrazin-5-one, 7-amino-2,3-dimethylpyrrolo[3,4-b]pyrazin -5-one, 7-amino-2,3-dihydro[1,4]dithiino[2,3-c]pyrrol-5-one, 3-amino-2-methyl-2,3-dihydroisoindol-1-one, 3-imino-2-ethyl-2,3-dihydroisoindol-1-one, 3-imino-2-propyl-2,3-dihydroisoindol-1-one, 2-hydroxymethyl-3-imino-2,3-dihydroisoindol- 1-one, 2-(2-hydroxyethyl)-3-imino-2,3-dihydroisoindol-1-one, 2-(1-imino-3-oxo-1,3-dihydroisoindol-2-yl)ethanesulphonic acid, 3-(1-imino-3-oxo-1,3-dihydroisoindol-2-yl)propionic acid, 2-(3-hydroxypropyl)-3-imino-2,3-dihydroisoindol-1-one and 5-imino-6-methyl-5,6-dihydropyrrolo[3,4-b]pyridin-7-one.

In the context of the present invention:

The halogen atoms preferentially denote a fluorine, chlorine, bromine or iodine atom.

The alkyl, monohydroxyalkyl, polyhydroxyalkyl, alkylhydroxyalkyl, alkylsulphonyl, carboxyalkyl, aminoalkyl, alkylaminoalkyl and dihydroxyaminoalkyl radicals can be linear or branched.

The alkyl groups in particular denote groups of 1 to 20 carbon atoms such as, for example, methyl, ethyl, propyl, isopropyl, n-propyl, butyl, n-butyl, tert-butyl, pentyl, n-pentyl, isopentyl, n-hexyl, iso-hexyl, heptyl, octyl, nonyl, decyl, undecyl, dodecyl and pentadecyl groups. The alkyl groups preferably denote a group of 1 to 6 carbon atoms; these alkyl groups can be substituted; for example, with a halogen atom or a cyano or hydroxyl radical, and can thus represent trifluoromethyl, δ-chloropropyl, β-cyanoethyl or β-hydroxyethyl radicals.

Among the Monohydroxyalkyl groups which may be mentioned in particular are hydroxymethyl, hydroxyethyl, hydroxypropyl and hydroxybutyl groups.

Among the polyhydroxyalkyl radicals which may be mentioned in particular are dihydroxyethyl, dihydroxypropyl, trihydroxypropyl and dihydroxybutyl radicals.

The alkoxy groups denote a group —O—R, R representing an alkyl group as defined above.

The alkenyl groups denote a monovalent radical corresponding to the ethylenic carbons, such as, for example, alkyl or 3,3-dimethylallyl.

The acetyloxy groups denote a group —O—CO—R, R representing an alkyl group as defined above.

Among the cycloalkyl radicals which may be mentioned in particular are cyclohexyl and cyclopentyl.

Among the aryl radicals, which may be mono- or polycyclic, mention may be made in particular of phenyl and naphthyl groups.

Among the heterocycles and in particular the 5- or 6-membered rings, which may be mono- or polycyclic and containing one or more hetero atoms, mention may be made of thiophene, pyrrole, imidazole, pyrazole, triazole, thiazole, furan, benzofuran, benzimidazole, benzothiazole, pyridyl, benzoxazole, quinolyl, quinazolyl, quinoxalyl, pyrrolidine, piperidine, piperazine and morpholine rings.

Among the alkylaryl radicals which may be mentioned in particular are benzyl, phenethyl and naphthyl methyl groups.

The aminoaryl groups denote groups $NH_2$—R, R representing an aryl radical.

In the context of the present invention, the cycloalkyl and aryl radicals and the heterocycles may be substituted or polysubstituted, for example with a halogen, with a $C_1$–$C_6$ alkyl or monohydroxyalkyl, a $C_2$–$C_6$ polyhydroxyalkyl radical, a $C_1$–$C_6$ alkoxy, a nitro group, a hydroxyl group, a carboxylic group, a $C_1$–$C_4$ acetyloxy group, a carboxamide group, a sulphonamide, sulphonic, nitrile, —$CF_3$ or —$OCF_3$ group, a cyano radical, a cyano($C_1$–$C_6$) alkyl radical, a $C_1$–$C_6$ alkoxy radical, a tri ($C_1$–$C_6$)alkylsilane($C_1$–$C_6$)alkyl radical, an amido radical, an aldehydo radical, a ($C_1$–$C_6$) alkylcarbonyl radical, a thio radical, a $C_1$–$C_6$ thioalkyl radical, a $C_1$–$C_6$ alkylthio radical, an amino radical or an amino radical protected with a ($C_1$–$C_6$)alkylcarbonyl, carbamyl or $C_1$–$C_6$ alkyl-sulphonyl radical.

In the context of the present invention, the formulae (I) to (VIII) are not limited to those specifically described, but also comprise the tautomeric forms thereof, when they exist.

For the purposes of the present invention, the cosmetically acceptable salts of the abovementioned compounds can be hydrochlorides, sulphates, hydrobromide or tartrates.

The compositions for dyeing keratin fibres, in particular human keratin fibres such as the hair, in accordance with the present invention are essentially characterized in that they comprise at least one aliphatic cationic amine as defined above and at least one compound chosen from an aldehyde, a ketone, a quinone and a diiminoisoindoline or 3-aminoisoindolone derivative as defined above, in a medium which is suitable for dyeing.

In one preferred embodiment of the invention, the compound chosen from an aldehyde, a ketone, a quinone and a diiminoisoindoline or 3-aminoisoindolone derivative is chosen from 1,4-dimethylaminobenzaldehyde and 4-dimethylaminonaphthaldehyde.

The aliphatic cationic amine can be present in a concentration ranging from 0.01% to 10% and preferably between 0.05% and 5% by weight relative to the total weight of the composition.

The compound chosen from an aldehyde, a ketone, a quinone and a diiminoisoindoline or 3-aminoisoindolone derivative can be present in a concentration ranging from 0.01% to 10% and preferably from 0.05% to 5% by weight relative to the total weight of the composition.

The medium which is suitable for dyeing is preferably an aqueous medium consisting of water and/or of cosmetically acceptable organic solvents, and more particularly alcohols such as ethyl alcohol, isopropyl alcohol, benzyl alcohol and phenylethyl alcohol, or glycols or glycol ethers such as propylene glycol or its ethers such as, for example, propylene glycol monomethyl ether, butylene glycol, dipropylene glycol and diethylene glycol alkyl ethers such as, for example, diethylene glycol monoethyl ether or monobutyl ether, in concentrations of between about 0.5% and 20%, and preferably between about 2% and 10%, by weight relative to the total weight of the composition.

Fatty amides such as mono- and diethanolamides of acids derived from copra, of lauric acid or of oleic acid can also be added to the composition according to the invention, in concentrations of between about 0.05% and 10% by weight.

Surfactants that are well known in the prior art and of anionic, cationic, nonionic, amphoteric or zwitterionic typo or mixtures thereof can also be added to the composition according to the invention, preferably in a proportion of between about 0.1% and 50% by weight and advantageously between about 1% and 20% by weight relative to the total weight of the composition.

Thickeners can also be used in a proportion ranging from about 0.2% to 20%.

The said dye composition can also contain various common adjuvants such as antioxidants, fragrances, sequestering agents, dispersants, hair conditioners, preserving agents and opacifiers, as well as any other additive usually used in the dyeing of keratin substances.

Needless to say, a person skilled in the art will take care to select the optional additional compounds mentioned above, such that the advantageous properties intrinsically associated with the dye composition according to the invention are not, or are not substantially, adversely affected by the addition(s) envisaged.

The dye composition according to the invention can be formulated at acidic, neutral or alkaline pH, it being possible for the pH to vary, for example, from 2 to 11 and preferably from 5 to 10, and it being possible for it to be adjusted by means of basifying or acidifying agents or buffers that are well known hitherto.

Basifying agents which may be mentioned are aqueous ammonia, alkaline carbonates, alkanolamines, for example mono-, di- and triethanolamine and derivatives thereof, sodium hydroxide, potassium hydroxide and the compounds of formula:

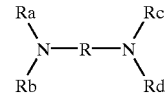

in which R is a propylene residue optionally substituted with a hydroxyl group or a $C_1$–$C_4$ alkyl radical; Ra, Rb, Rc and Rd, simultaneously or independently of each other, represent a hydrogen atom or a $C_1$–$C_4$ alkyl or $C_1$–$C_4$ hydroxyalkyl radical.

The acidifying agents are conventionally mineral or organic acids such as, for example, hydrochloric acid, tartaric acid, citric acid and phosphoric acid.

Among the buffers which may be mentioned, for example, is potassium dihydrogen phosphate/sodium hydroxide.

The composition applied to the hair can be in various forms, such as in the form of a liquid, cream or gel or in any other form which is suitable for dyeing keratin fibres. In particular, it can be packaged under pressure in an aerosol can in the presence of a propellant and can form a mousse.

In accordance with the present invention, the process for dyeing keratin fibres, in particular human keratin fibres such as the hair, is essentially characterized in that a component (A) consisting of a composition containing, in a medium which is suitable for dyeing, at least one cationic amine such as for example a compound such as these defined above, and a component (B) consisting of a composition containing, in a medium which is suitable for dyeing, at least one compound chosen from an aldehyde, a ketone, a quinone and a diiminoisoindoline or 3-aminoisoindolone derivative such as, for example, one of the those defined above, is applied to the said fibres so as to allow the development of a coloration on the said keratin fibres.

In one preferred embodiment of the process of the invention, the components (A) and (n) are mixed together just before use, and the resulting composition is then applied immediately to the keratin fibres, and is left to act on them for 1 to 60 minutes and preferably from 1 to 30 minutes; the keratin fibres then being rinsed, washed with shampoo, rinsed again and then dried.

Another process of the present invention consists essentially in applying component (A) to the keratin fibres, followed or preceded by application of component (B) to the said fibres, in leaving each component to act for 1 to 60 minutes and preferably from 1 to 30 minutes, and optionally in rinsing with water between each application; the keratin fibres then being rinsed, washed with shampoo, rinsed again and then dried.

A subject of the invention is also an agent for dyeing keratin fibres, in particular human hair, characterized in that it consists of components (A) and (B) stored separately, as defined above.

Components (A) and (B) are intended either to be mixed together immediately before use or to be applied successively to the fibres to be treated.

According to one embodiment, the various components (A) and (B) can be packaged in a multi-compartment device also known as a "dyeing kit" comprising all the components intended to be applied for the same dyeing operation on the keratin fibres, in particular human keratin fibres such as the hair, in successive applications with or without premixing.

Such devices can comprise a first compartment containing component (A) containing the aliphatic cationic amine and a second compartment containing component (B) containing the compound chosen from an aldehyde, a ketone, a quinone and a diiminoisoindoline or 3-aminoisoindolone derivative.

Another variant can also consist in storing component (A) or component (B) in an anhydrous solvent medium and in providing a third compartment containing a cosmetically acceptable aqueous medium which is suitable for dyeing. In this case, the contents of the third compartment are mixed, immediately before use, into one or other or both of the compartments containing the anhydrous components (A) and (B), or alternatively the three compartments are mixed together before use.

Concrete examples illustrating the invention will now be given.

EXAMPLE 1

The dye composition below was prepared just before use;

| | |
|---|---|
| 1H-indole-2,3-dione ($3 \times 10^{-3}$ mol) | 0.441 g |
| [2-(4-aminophenylamino)ethyl]diethylmethylammonium chloride hydrochloride ($3 \times 10^{-3}$ mol) | 0.99 g |
| ethyl alcohol | 20 |
| triethanolamine | qs pH 7 |
| water | qs 100 g |

The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent-waved grey hair |
|---|---|---|
| red-copper | red-copper | red-copper |

These colorations withstand shampoo-washing particularly well.

EXAMPLE 2

The dye composition below was prepared just before use:

| | |
|---|---|
| 1H-indole-2,3-dione ($3 \times 10^{-3}$ mol) | 0.441 g |
| [2-(4-aminophenylamino)ethyl]diethylmethylammonium chloride hydrochloride ($3 \times 10^{-3}$ mol) | 0.99 g |
| ethyl alcohol | 20 g |
| triethanolamine | qs pH 4 |
| water | qs 100 g |

The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent-waved grey hair |
|---|---|---|
| coppery | red-copper | coppery |

These colorations withstand shampooing particularly well.

EXAMPLE 3

The dye composition below was prepared just before use:

| | |
|---|---|
| 1H-indole-2,3-dione ($3 \times 10^{-3}$ mol) | 0.441 g |
| [2-(2,5-diaminophenoxy)ethyl]diethylmethylammonium chloride hydrochloride ($3 \times 10^{-3}$ mol) | 1.09 g |
| ethyl alcohol | 20 g |
| triethanolamine | qs pH 7 |
| water | qs 100 g |

The above composition was applied at room temperature to permanent-waved or non-permanent-waved natural grey hair, or to bleached hair, at a rate of 5 grams per gram of hair. The hair was then rinsed with running water and dried.

The colorations obtained are indicated in the table below:

| Natural grey hair | Bleached hair | Permanent-waved grey hair |
|---|---|---|
| rosewood | light chestnut | light chestnut |

These colorations withstand shampooing particularly well.

EXAMPLE 4

The dye composition below was prepared just before use:

| | |
|---|---|
| 1H-indole-2,3-dione ($3 \times 10^{-3}$ mol) | 0.441 g |
| [2-(2,5-diaminophenoxy)ethyl]diethylmethylammonium chloride hydrochloride ($3 \times 10^{-3}$ mol) | 1.09 g |
| ethyl alcohol | 20 g |
| triethanolamine | qs pH 4 |
| water | qs 100 g |

The above composition was applied at room temperature to permanent-waved or non-permanent-waved natural grey hair, or to bleached hair, at a rate of 5 grams per gram of hair. The hair was then rinsed with running water and dried.

The Colorations obtained are indicated in the table below:

| Natural grey hair | Bleached hair | Permanent-waved grey hair |
|---|---|---|
| pink-beige | deep rosewood | rosewood |

These colorations are fast in particular with respect to shampooing.

What is claimed is:

1. A process for dyeing at least one keratin fiber comprising applying to said at least one fiber a composition comprising:

(a) at least one compound chosen from aldehydes; ketones; quinones; diiminoisoindoline derivatives; and 3-aminoisoindolone derivatives; and (b) at least one aliphatic cationic amine chosen from amines having formula (I) and the cosmetically acceptable salts thereof:

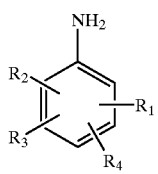 (I)

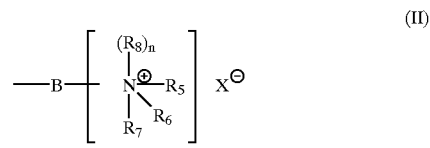 (II)

wherein:

R₁, R₂, R₃ and R₄, which may be identical or different, are each chosen from hydrogen; halogens; —NH₂ groups; —OH groups; —Z groups; —COZ groups; —COOZ groups; alkylcarbonyl groups; aminoalkylcarbonyl groups; N-alkylaminoalkylcarbonyl groups; N,N-dialkylaminoalkylcarbonyl groups; aminoalkylcarbonylalkyl groups; N-alkylaminoalkylcarbonylalkyl groups; N,N-dialkylaminoalkylcarbonylalkyl groups; carboxyl groups; alkylcarboxyl groups; alkylsulphonyl groups; aminosulphonyl groups; N-alkylaminosulphonyl groups; N,N-dialkylaminosulphonyl groups; aminosulphonylalkyl groups; N-alkylaminosulphonylalkyl groups; N,N-dialkylaminosulphonylalkyl groups; carbamyl groups; N-alkylcarbamyl groups; N,N-dialkylcarbamyl groups; carbamylalkyl groups; N-alkylcarbamylalkyl groups; N,N-dialkylcarbamylalkyl groups; alkyl groups; monohydroxyalkyl groups; polyhydroxyalkyl groups; alkoxyalkyl groups; trifluoroalkyl groups; cyano groups; —OR$_i$ groups; —SR$_i$ groups; —OR$_i$Z groups; —SR$_i$Z groups; and amino groups protected with at least one group chosen from alkylcarboxyl groups, trifluoroalkylcarbonyl groups, aminoalkylcarbonyl groups, carbonyl groups, N-alkylaminoalkylcarbonyl groups, N,N-dialkylaminoalkylcarbonyl groups, alkylcarboxyl groups, carbamyl groups, N-alkylcarbamyl groups, N,N-dialkylcarbamyl groups, alkylsulphonyl groups, aminosulphonyl groups, N-alkylaminosulphonyl groups, N,N-dialkylaminosulphonyl groups, thiocarbamyl groups, formyl groups, —COZ groups, and —COOZ groups;

wherein

R$_i$, which may be identical or different, are each chosen from alkyl groups; monohydroxyalkyl groups; polyhydroxyalkyl groups; —Z groups; alkoxyalkyl groups; aryl groups; benzyl groups; carboxyalkyl groups; alkylcarboxyalkyl groups; cyanoalkyl groups; carbamylalkyl groups; N-alkylcarbamylalkyl groups; N,N-dialkylcarbamylalkyl groups; trifluoroalkyl groups; aminosulphonylalkyl groups; N-alkylaminosulphonylalkyl groups; N,N-dialkylaminosulphonylalkyl groups; alkylsulphinylalkyl groups; alkylsulphonylalkyl groups; alkylcarbonylalkyl groups, aminoalkyl groups; and aminoalkyl groups in which said amine is substituted with at least one group chosen from alkyl groups, monohydroxyalkyl groups, polyhydroxyalkyl groups, alkylcarbonyl groups, formyl groups, trifluoroalkylcarbonyl groups, alkylcarboxyl groups, carbamyl groups, N-alkylcarbamyl groups, N,N-dialkylcarbamyl groups, thiocarbamyl groups, alkylsulphonyl groups, —Z groups, —COZ groups, and —COOZ groups;

Z, which may be identical or different, are each chosen from groups having formula (II).

wherein:

B, which may be identical or different, are each chosen from linear divalent alkyl groups and branched divalent alkyl groups, optionally interrupted by at least one heteroatom, and optionally substituted with at least one group chosen from hydroxyl and C₁–C₆ alkoxy groups;

R₅, R₆ and R₇, which may be identical or different, are each chosen from alkyl groups; monohydroxyalkyl groups; polyhydroxyalkyl groups; alkoxyalkyl groups; cyanoalkyl groups; aryl groups; benzyl groups; carbamylalkyl groups; trialkylsilane alkyl groups; and aminoalkyl groups wherein said amine is protected with at least one group chosen from alkylcarbonyl groups, carbamyl groups, and alkylsulphonyl groups;

two of R₅, R₆ and R₇, may also form, together with the nitrogen atom to which they are attached, at least one ring, optionally substituted, chosen from 5-membered rings and 6-membered rings, wherein said at least one ring comprises at least one heteroatom; and at least one of R₅, R₆ and R₇, which may be identical or different, may also be chosen from —B' groups of a second 'Z group, wherein said —B' groups are chosen from —B groups;

X$^\ominus$, which may be identical or different, are each chosen from monovalent anions and divalent anions;

R₈, which may be identical or different, are each chosen from alkyl groups; monohydroxyalkyl groups; polyhydroxyalkyl groups; aryl groups; benzyl groups; aminoalkyl groups; aminoalkyl groups wherein said amine is protected with at least one group chosen from alkylcarbonyl groups, carbamyl groups and alkylsulphonyl groups; carboxyalkyl groups; cyanoalkyl groups; carbamylalkyl groups; trifluoroalkyl groups; trialkylsilane alkyl groups; sulfonamidoalkyl groups; alkylcarboxyalkyl groups; alkylsulfinylalkyl groups; alkylsulfonylalkyl groups; alkylketoalkyl groups, N-alkylcarbamylalkyl groups; and N-alkylsulfonamidoalkyl groups;

n is an integer chosen from 0 and 1, with the proviso that, when n=0, B is attached to the nitrogen atom substituted with R₅, R₆ and R₇;

when n=1, two of R₅, R₆ and R₇ form, together with the nitrogen atom to which they are attached, at least one saturated ring, optionally substituted, chosen from 5-membered heterocycles and 6-membered heterocycles, wherein said at least one saturated ring comprises at least one heteroatom, and B is attached to at least one carbon atom of said at least one saturated ring; and with the proviso that in said amine of formula (I), at least one of R₁, R₂, R₃, and R₄ comprises at least one Z group;

wherein a coloration of said at least one keratin fiber is achieved without an oxidizing agent.

2. A process according to claim 1, wherein said at least one keratin fiber is a human keratin fiber.

3. A process according to claim 2, wherein said human keratin fiber is hair.

4. A process according to claim 1, wherein said at least one heteroatom is chosen from oxygen; sulphur; and nitrogen.

5. A process according to claim 1, wherein said monovalent and divalent anions are chosen from halogens; hydroxide anions; hydrogen sulphate anions; and alkyl sulphate anions.

6. A process according to claim 5, wherein said halogens are chosen from chlorine, bromine, fluorine and iodine.

7. A process according to claim 5, wherein said alkyl sulphate anions are chosen from methyl sulphate and ethyl sulphate.

8. A process according to claim 1, wherein said at least one compound is chosen from aldehydes having the formula (III) and the cosmetically acceptable salts thereof:

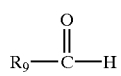
(III)

in which $R_9$ is chosen from groups having formula (III A):

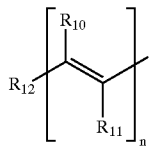
(III A)

in which:

- $R_{10}$ and $R_{11}$, which may be identical or different, are each chosen from hydrogen; alkyl groups; monohydroxyalkyl groups; polyhydroxyalkyl groups; alkylhydroxyalkyl groups; alkoxy groups; —$CF_3$ groups; and —$OCF_3$ groups;
- $R_{10}$ and $R_{11}$, which may be identical or different, may also form, together with the atoms to which they are attached, at least one ring, optionally substituted, chosen from aryl rings; 5-membered heterocyclic rings; and 6-membered heterocyclic rings;
- n is an integer ranging from 0 to 3; and
- $R_{12}$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered heterocyclic groups, optionally substituted.

9. A process according to claim 1, wherein said at least one compound is chosen from ketones having formula (IV), ketones having formula (V), and the cosmetically acceptable salts thereof:

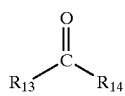
(IV)

-continued

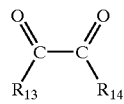
(V)

in which $R_{13}$ is chosen from groups having formula (III A):

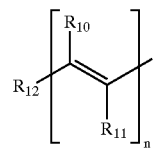
(III A)

in which:

- $R_{10}$ and $R_{11}$, which may be identical or different, are each chosen from hydrogen; alkyl groups; monohydroxyalkyl groups; polyhydroxyalkyl groups; alkylhydroxyalkyl groups; alkoxy groups; —$CF_3$ groups; and —$OCF_3$ groups;
- $R_{10}$ and $R_{11}$, which may be identical or different, may also form, together with the atoms to which they are attached, at least one ring, optionally substituted, chosen from aryl rings; 5- membered heterocyclic rings; and 6-membered heterocyclic rings;
- n is an integer ranging from 0 to 3; and
- $R_{12}$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered heterocyclic groups, optionally substituted;
- $R_{14}$ is chosen from alkyl groups; monohydroxyalkyl groups; polyhydroxyalkyl groups; alkylhydroxyalkyl groups; aryl groups, optionally substituted; alkylaryl groups, optionally substituted; 5-membered heterocyclic groups, optionally substituted; and 6-membered heterocyclic groups, optionally substituted;
- $R_{13}$ and $R_{14}$ may also form, together with the atoms to which they are attached, at least one ring, optionally substituted, chosen from 5-membered aryl rings, 6-membered aryl rings, and heterocyclic rings, it being possible for said at least one ring itself to be attached to at least one ring, optionally substituted, chosen from 5-membered aryl rings, 6-membered aryl rings, and heterocyclic rings.

10. A process according to claim 9, wherein said heterocyclic rings comprise at least one heteroatom chosen from N and S.

11. A process according to claim 1, wherein said at least one compound is chosen from quinones having formula (VI), quinones having formula (VII), and the cosmetically acceptable salts thereof:

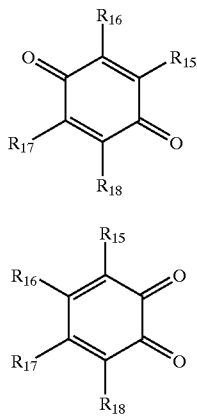

(VI)

(VII)

in which:
- $R_{15}$ is chosen from hydrogen; halogens; sulphonic groups; and alkoxy groups;
- $R_{16}$, $R_{17}$ and $R_{18}$, which may be identical or different, are each chosen from hydrogen; halogens; hydroxyl groups; alkyl groups; monohydroxyalkyl groups; polyhydroxyalkyl groups; alkylhydroxyalkyl groups; alkylsulphonyl groups; carboxyalkyl groups; aminoalkyl groups; alkylaminoalkyl groups; (dihydroxy)alkylaminoalkyl groups; alkyl-NR'R" groups, wherein R' and R", which may be identical or different, are each chosen from alkyl groups, or R' and R" may also form, together with the nitrogen atom to which they are attached, at least one ring chosen from aryl rings, 5-membered heterocycles and 6-membered heterocycles; aryl groups; amino groups, optionally substituted with at least one group chosen from alkyl groups and hydroxyalkyl groups; and
- at least one of $R_{15}$ and $R_{16}$, $R_{16}$ and $R_{17}$, and $R_{17}$ and $R_{18}$ may also form, together with the atoms to which they are attached, at least one ring, optionally substituted, chosen from aryl rings, 5-membered heterocycles, and 6-membered heterocycles.

12. A process according to claim 1, wherein said at least one compound is chosen from diaminoisoindolines having formula (VIII), 3-aminoisoindolone derivatives having formula (VIII), and the cosmetically acceptable salts thereof:

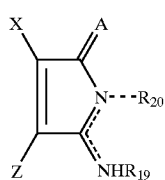

(VIII)

in which:
- $R_{19}$ and $R_{20}$, which may be identical or different, are each chosen from hydrogen; alkyl groups; monohydroxyalkyl groups; polyhydroxyalkyl groups; alkylhydroxyalkyl groups; aminoalkyl groups; alkylaminoalkyl groups; (dihydroxy)alkylaminoalkyl groups; and alkyl-NR'R" groups, wherein R' and R", which may be identical or different, are each chosen from alkyl groups, or R' and R" may also form, together with the nitrogen atom to which they are attached, at least one ring chosen from aryl rings, 5-membered heterocycles, and 6-membered heterocycles;

A is chosen from oxygen and NH; and
X and Z form, together with the atoms to which they are attached, at least one ring, optionally substituted, chosen from aryl rings, 5-membered heterocycles, and 6-membered heterocycles.

13. A process according to claim 1, wherein said at least one aliphatic cationic amine is chosen from:
[2-(2,4-diaminophenoxy)ethyl]diethylmethylammonium chloride;
[3-(2,4-diaminophenoxy)propyl]triethylammonium chloride;
[2-(2,4-dihydroxyphenyl)-2-oxoethyl]triethylammonium chloride;
[2-(4-amino-2-hydroxyphenoxy)ethyl] diethylmethylammonium chloride;
triethyl[2-(3-hydroxy-4-methylphenylamino)ethyl] ammonium bromide;
triethyl[2-(3-hydroxy-2,4-dimethylphenylcarbamoyloxy)ethyl]ammonium chloride;
[2-(4-chloro-5-hydroxyphenylamino)ethyl] triethylammonium bromide;
[2-(2,4-diaminophenoxy)ethyl]diethylmethylammonium chloride;
[2(2,4-diaminophenyl)ethyl]triethylammonium chloride;
triethyl[(3-hydroxy-4-methylphenylcarbamoyl) methylammonium chloride;
[2-[4-(dimethylamino)salicylamido]ethyl] diethylmethylammonium iodide;
ethyl(2-hydroxyethyl)dimethylammonium 4-(methylamino)salicylate bromide;
3-[(4-amino-2-hydroxybenzoyl)oxy]-N-ethyl-N,N-dimethyl-1-propylammonium iodide;
3-[(4-amino-2-hydroxybenzoyl)oxy]-N,N,N-trimethyl-1-propylammonium iodide;
triethyl(2-hydroxyethyl)ammonium 4-aminosalicylate bromide;
2-[(4-amino-2-hydroxybenzoyl)oxy]-N,N-diethyl-N-methylethylammonium iodide;
2-[(4-amino-2-hydroxybenzoyl)oxy]-N-ethyl-N,N-dimethylethylammonium iodide;
ethyl(2-hydroxyethyl)dimethylammonium 4-aminosalicylate bromide;
2-[(4-amino-2-hydroxybenzoyl)oxy]-N,N,N-trimethylethylammonium iodide;
{2-[2-aminophenylamino]ethyl}trimethylammonium monochloride monohydrate;
[2-(2-amino-5-chlorophenylamino)ethyl] trimethylammonium monochloride;
[2-(2-amino-6-chlorophenylamino)ethyl] trimethylammonium monochloride;
[2-(2-amino-4-chlorophenylamino)ethyl] trimethylammonium monochloride;
{2-[2-amino-4-chloro-5-(2-hydroxyethoxy)phenylamino]ethyl}trimethylammonium monochloride;
[2-(2-amino-5-methoxyphenylamino)ethyl] trimethylammonium monochloride;
[2-(2-amino(2-hydroxyethyl)phenylamino)ethyl] dimethylammonium monobromide;
[3-(2-aminophenylamino)propyl]diethylmethylammonium monochloride;
[2-(2-amino-4-methylphenylamino)ethyl] trimethylammonium monochloride;
[2-(2,5-diaminophenoxy)ethyl]diethylmethylammonium chloride monohydrate;
N,N-bis(trimethylammoniumpropyl)-4-aminoaniline dichloride;
[4-(4-aminophenylamino)pentyl]diethylmethylammonium chloride;

[4-(4-aminophenylamino)pentyl]diethyl(2-hydroxyethyl) ammonium chloride;
[2-(4-aminophenylamino)ethyl]diethylmethylammonium chloride;
{2-[(4-aminophenyl)methylamino]ethyl}trimethylammonium chloride;
and the acid addition salts thereof.

14. A process according to claim 1, wherein said at least one aliphatic cationic amine is chosen from:
[3-(4-aminophenylamino)propyl]trimethylammonium chloride;
[2-(4-aminophenylamino)propyl]trimethylammonium chloride;
[4-(4-amino-2-methylphenylamino)pentyl] diethylmethylammonium chloride;
[4-(4-amino-3-methylphenylamino)pentyl] diethylmethylammonium chloride;
N1, N4-bis[3-N-methyl-N-(4'-aminoaniline)ethyl]-1,1,4,4-tetramethyldiammonium 1,3-propane dibromide dihydrabromide propane dibromide monohydrate;
N1, N3-bis[3-N(4'-aminoaniline)propyl]-1,1,3,3-tetramethyldiammonium 1,3-propane dibromide monohydrate;
1,3-bis{[2-(4-aminoaniline)propyl]-1,1,3,3-tetramethyldiammoniumpropane dibromide;
1,3-bis{[4-(4-aminoaniline)pentyl]-1,1,3,3-tetramethyldiammoniumpropane dichloride;
[4-(4-aminophenylamino)pentyl](5-amino-2-hydroxybenzyl)diethylammonium monochloride;
[2-(4-aminophenylamino)propyl](5-amino-2-hydroxybenzyl)dimethylammonium monochloride;
N1, N3-bis[3-N-(2'-aminoaniline)propyl]-1,1,3,3-tetramethyldiammonium 1,3-propane dibromide;
1,3-bis{[2-(2,4-diaminophenoxy)ethyl] diethylammonium}propane dibromide;
and the acid addition salts thereof.

15. A process according to claim 1, wherein said at least one compound is chosen from benzaldehyde; 2-monohydroxybenzaldehyde; 3-monohydroxybenzaldehyde; 4-monohydroxybenzaldehyde; 2-monomethoxybenzaldehyde; 3-monomethoxybenzaldehyde; 4-monomethoxybenzaldehyde; 2-monomethylbenzaldehyde; 3-monomethylbenzaldehyde; 4-monomethylbenzaldehyde; (2,3)-dihydroxybenzaldehyde; (2,4)-dihydroxybenzaldehyde; (2,5)-dihydroxybenzaldehyde; (2,6)-dihydroxybenzaldehyde; (3,5)-dihydroxybenzaldehyde; (2,3)-dimethoxybenzaldehyde; (2,4)-dimethoxybenzaldehyde; (2,5)-dimethoxybenzaldehyde; (2,6)-dimethoxybenzaldehyde; (3,5)-dimethoxybenzaldehyde; vanillin; isovanillin; syringaldehyde; orthophthalaldehyde; isophthalaldehyde; terephthalaldehyde; (2,3)-dimethylbenzaldehyde; (2,4)-dimethylbenzaldehyde; (2,5)-dimethylbenzaldehyde; (2,6)-dimethylbenzaldehyde; (3,5)-dimethylbenzaldehyde; 4-isopropylbenzaldehyde; 4-dimethylaminobenzaldehyde; 4-diethylaminobenzaldehyde; piperonal; (2,6)-dimethyl-4-hydroxybenzaldehyde; (3,5)-dimethyl-4-hydroxybenzaldehyde; 2-mononitrobenzaldehyde; 3-mononitrobenzaldehyde; 4-mononitrobenzaldehyde; 2-hydroxy-3-methoxybenzaldehyde; 2-hydroxy-4-methoxybenzaldehyde; 2-hydroxy-5-methoxybenzaldehyde; 2-hydroxy-6-methoxybenzaldehyde; 4-methylthiobenzaldehyde; (2,3,4)-trihydroxybenzaldehyde; (2,4,6)-trihydroxybenzaldehyde; (3,4,5)-trihydroxybenzaldehyde; (2,4,5)-trihydroxybenzaldehyde; methyl 2-formyl benzoate; methyl 3-formyl benzoate; methyl 4-formyl benzoate; 2-mono(2-hydroxyethoxy)benzaldehyde; 3-mono(2-hydroxyethoxy) benzaldehyde; 4-mono(2-hydroxyethoxy)benzaldehyde; 4-nitro-3-hydroxybenzaldehyde; 3-nitro-4-hydroxybenzaldehyde; 2-nitro-4-hydroxybenzaldehyde; 3-nitro-2-hydroxybenzaldehyde; 2-monotrifluorobenzaldehyde; 3-monotrifluorobenzaldehyde; 4-monotrifluorobenzaldehyde; 2,3-dihydroxy-4-methoxybenzaldehyde; 3,4-dihydroxy-5-methoxybenzaldehyde; 3,5-dihydroxy-4-methoxybenzaldehyde; 3-methoxy-2-nitrobenzaldehyde; 4-methoxy-2-nitrobenzaldehyde; 2-methoxy-3-nitrobenzaldehyde; 4-methoxy-3-nitrobenzaldehyde; (2,3,4)-trimethoxybenzaldehyde; (2,4,6)-trimethoxybenzaldehyde; (3,4,5)-trimethoxybenzaldehyde; (2,4,5)-trimethoxybenzaldehyde; 5-nitrovanillin; (2,4)-dinitrobenzaldehyde; (2,6)-dinitrobenzaldehyde; pentamethylbenzaldehyde; 4-methylsulphonylbenzaldehyde; 2-monoformylphenoxyacetic acid; 3-monoformylphenoxyacetic acid; 4-monoformylphenoxyacetic acid; 4-diethylaminosalicylaldehyde; 4-(3-dimethylaminopropoxy)benzaldehyde; 2,3dihydrobenzo(b)furan-5-carboxaldehyde; 1-naphthaldehyde; 2-naphthaldehyde; 6-carboxaldehyde-1,4-benzodioxane; 5-carboxaldehyde-1,4-benzodioxane; 2-monohydroxy-1-naphthaldehyde; 4-monohydroxy-1-naphthaldehyde; 1-monohydroxy-2-naphthaldehyde; 1-(4-formylphenyl)imidazole; 4-pyrrolidinobenzaldehyde; 2-monomethoxy-1-naphthaldehyde; 4-monomethoxy-1-naphthaldehyde; 2,3-dimethylchroman-6-carboxaldehyde; 2,3,6,7-tetrahydro-1H,5H-pyrido(3,2,1-IJ)quinoline-9-carbaldehyde; 4-dimethylamino-1-naphthaldehyde; 9-anthraldehyde; 3-nitro-4-pyrrolidinobenzaldehyde; 3-nitro-4-piperidinobenzaldehyde; 3-nitro-4-morpholinobenzaldehyde; pyridine-2-monocarboxaldehyde; pyridine-3-monocarboxaldehyde; pyridine-4-monocarboxaldehyde; 2,6-pyridinodicarboxaldehyde; 5-formyl-6-methyluracil; pyridoxal; quinoline-2-monocarboxaldehyde; quinoline-3-monocarboxaldehyde; quinoline-4-monocarboxaldehyde; 8-hydroxyquinoline-2-carboxaldehyde; 2-furaldehyde; 3-furaldehyde; 2-thienylcarboxaldehyde; 3-thienylcarboxaldehyde; 2-imidazocarboxaldehyde; 3-imidazocarboxaldehyde; 2-pyrrolecarboxaldehyde; 5-nitro-2-furaldehyde; 5-(dimethylamino)-2-furaldehyde; 2,5-thiophenedicarboxaldehyde; 2,3-thiophenedicarboxaldehyde; pyrazole-3-carbaldehyde; 5-nitro-2-thiophenecarboxaldehyde; 5-nitro-3-thiophenecarboxaldehyde; indole-3-carboxaldehyde; N-methylindole-3-carboxaldehyde; 2-methylindole-3-carboxaldehyde; 4-monomethylindolecarboxaldehyde; 5-monomethylindolecarboxaldehyde; 6-monomethylindolecarboxaldehyde; 7-monomethylindolecarboxaldehyde; and 5-formyl-2-furansulphonic acid.

16. A process according to claim 1, wherein said at least one compound is chosen from 2,3-indolinedione; 2,3-butanedione; 2,3-pentanedione; (2,3)-hexanedione; (3,4)-hexanedione; 1-phenyl-1,2-propanedione; benzil; furil; 2,2'-pyridil; nitrobenzil; anisil; 3,3'-dimethoxybenzil; 4,4'-bis (dimethyl amino)benzil; camphoroquinone; cyclohexane-1,2-dione; isatin; N-methylisatin; 4-monomethylisatin; 5-monomethylisatin; 6-monomethylisatin;

7-monomethylisatin; (4,5)-dimethylisatin; (4,7)-dimethylisatin; (5,7)-dimethylisatin; (6,7)-dimethylisatin; N-ethylisatin; N-hydroxymethylisatin; 5-monomethoxyisatin; 6-monomethoxyisatin; 7-monomethoxyisatin; 4-monochloroisatin; 5-monochloroisatin; 6-monochloroisatin; 7-monochloroisatin; 4-monobromoisatin; 5-monobromoisatin; 6-monobromoisatin; 7-monobromoisatin; N-isopropylisatin; N-butylisatin; N-propylisatin; 5-nitroisatin; isatin-5-sulphonic acid; 2,4,5-trihydroxypyrimidine; alloxan; 1,3-dimethylhexahydro-2,4,5,6-pyrimidinetetraone; ninhydrin; chinisatin; 1,3-indenedione; squaric acid; croconic acid; 3,4-dimethoxy-3-cyclobutene-1,2-dione; 3-ethoxy-3-cyclobutene-1,2-dione; 4-ethoxy-3-cyclobutene-1,2-dione; 3-isopropoxy-3-cyclobutene-1,2-dione; 4-isopropoxy-3-cyclobutene-1,2-dione; 3,4-di-N-butoxy-3-cyclobutene-1,2-dione; rhodizonic acid; oxindole; N-methyl-2-indolinone; N-methylnitro-2-indolinone; 6methoxyoxindole; 5,6-dimethoxyoxindole; 5-monochlorooxindole; and 6-monochlorooxindole.

17. A process according to claim 1, wherein said at least one compound is chosen from 1,4-naphthoquinone; spinulosin; atromentin; aurentioglyocladin; 2,5-dihydroxy-6-methylbenzoquinone; 2-hydroxy-3-methyl-6-methoxybenzoquinone; 2,5-dihydroxy-3,6-diphenylbenzoquinone; 2,3-dimethyl-5-hydroxy-6-methoxybenzoquinone; 2,5-dihydroxy-6-isopropylbenzoquinone; lawsone; juglone; fafioline; naphthazarine; naphthopurpurine; lapachol; plumbagin; chloroplumbagin; droserone; shikonine; 2-hydroxy-3-methyl-1,4-naphthoquinone; 3,5-dihydroxy-1,4-naphthoquinone; 2,5-dihydroxy-1,4-naphthoquinone; 2-methoxy-5-hydroxy-1,4-naphthoquinone; 3-methoxy-5-hydroxy-1,4-naphthoquinone; (1,4)-naphthoquinone; (1,2)-naphthoquinone; 4,5-dimethoxy-1,2-benzoquinone; phenanthrenequinone; and (1,2)-naphtho-quinone-4-sulphonic acid.

18. A process according to claim 1, wherein said at least one compound is chosen from 3-imino-3H-isoindolylamine; 3-imino-4-methyl-3H-isoindol-1-ylamine; 3-imino-4-tert-butyl-3H-isoindol-1-ylamine; 3-imino-7-nitro-3H-isoindol-1-ylamine; 3-amino-1-imino-1H-isoindol-4-ol; 3-imino-7-isopropoxy-3H-isoindol-1-ylamine; 3-imino-7-(2,2,2-trifluoroethoxy)-3H-isoindol-1-ylamine; 3-imino-7-ethoxy-3H-isoindol-1-ylamine; 3-imino-7-butoxy-3H-isoindol-1-ylamine; 3-amino-1-imino-1 H-isoindole-4-sulphonic acid; 3-imino-7-chloro-3H-isoindol-1-ylamine; 3-imino-5-methyl-3H-isoindol-1-ylamine; 3-imino-5-ethyl-3H-isoindol-1 -ylamine; 3-imino-5-tert-butyl-3H-isoindol-1-ylamine; 3-imino-5-amino-3H-isoindol-1-ylamine; N-(1-amino-3-imino-3H-isoindol-5-yl)acetamide; 3-imino-5-nitro-3H-isoindol-1-ylamine; 3-imino-5-fluoro-3H-isoindol-1-ylamine; 3-imino-5-chloro-3H-isoindol-1-ylamine; 3-imino-5-methylsulphonyl-3H-isoindol-1-ylamine; 3-imino-5-methoxy-3H-isoindol-1-ylamine; 3-imino-5-ethoxy-3H-isoindol-1-ylamine; 3-imino-5-propoxy-3H-isoindol-1-ylamine; 3-imino-5-isopropoxy-3H-isoindol-1-yl-amine; 3-imino-5-butoxy-3H-isoindol-1-ylamine; 3-imino-5-isobutoxy-3H-isoindol-1-ylamine; 3-imino-5-tert-butoxy-3H-isoindol-1-ylamine; 3-imino-5-(2,2,2-trifluoromethyl)-3H-isoindol-1-ylamine; 3-imino-5-(2,2,2-trifluoroethoxy)-3H-isoindol-1-ylamine; 3-imino-5-methanesulphonyl-3H-isoindol-1-ylamine; 3-imino-5,6-dimethyl-3H-isoindol-1-ylamine; 3-imino-5,6-diethyl-3H-isoindol-1-ylamine; 3-imino-5,6-dimethoxy-3H-isoindol-1-ylamine; 3-imino-5,6-diethoxy-3H-isoindol-1-ylamine; 3-imino-5,6-dibutoxy-3H-isoindol-1-ylamine; 3-imino-5,6-bis(trifluoromethyl)-3H-isoindol-1-ylamine; 3-imino-5,6-dichloro-3H-isoindol-1-ylamine; 5,6-bis(ethoxymethyl)3-imino-3H-isoindol-1-ylamine; 3-amino-1-imino-1H-isoindole-4,7-diol; 4,7-dichloro-3-imino-3H-isoindol-1-ylamine; 4,5,7-trichloro-3-imino-N6,N6-dimethyl-3H-isoindole-1,6-diamine; 4,5,6,7-tetrachloro-3-imino-3H-isoindol-1-ylamine; 4,5,6,7-tetrafluoro-3-imino-3H-isoindol-1-ylamine; 3-butylimino-3H-isoindol-1-ylamine; 2-(3-aminoisoindol-1-ylideneamino)ethanol; 3-(3-aminoisoindol-1-ylideneamino)-3-methylpentane-1,5-diol; N-(3-aminoisoindol-1-ylidene)guanidine; 7-imino-7H-pyrrolo[3,4-b]pyrid-5-ylamine; 7-imino-7H-pyrrolo[3,4-b]pyrazin-5-ylamine; 7-imino-2,3-dimethyl-7H-pyrrolo[3,4-b]pyrazin-5-ylamine; 7-imino-7H-[1,4]dithiino[2,3-c]pyrrol-5-ylamine; 7-imino-2,3-dimethyl- 7H-[1,4]dithiino[2,3-c]pyrrol-5-ylamine; 7-imino-2,3-dihydro-7H-[1,4]dithiino[2,3 -c]pyrrol-5-ylamine; 7-imino-2-methyl-2,3-dihydro-7H-[1,4]dithiino[2,3-c]pyrrol-5-ylamine; 3-aminoisoindol-1-one; 3-amino-7-methylisoindol-1-one; 3-amino-7-hydroxymethylisoindol-1-one; 3-amino-7-chloroisoindol-1-one; 3-amino-4-chloroisoindol-1-one; 3-amino-1-oxo-1H-isoindole-4-sulphonic acid; 3-amino-4-nitroisoindol-1-one; 3-amino-6-nitroisoindol-1-one; 3-amino-6-methylisoindol-1-one; 3-amino-6-chloro-isoindol-1-one; 3-amino-6-bromo-isoindol-1-one; 3-amino-6-methylsulphanylisoindol-1-one; 3-amino-6-methoxyisoindol-1-one; 3-amino-5-chloroisoindol-1-one; 3-amino-5-fluoroisoindol-1-one; 3-amino-5-methoxyisoindol-1-one; 3-amino-5-nitroisoindol-1-one; ethyl 3-amino-1-oxo-1H-isoindole-5-carboxylate; 3-amino-5,6-dichloroisoindol-1-one; 3-amino-5,6-dibromoisoindol-1-one; 3-amino-4,7-dichloroisoindol-1-one; 3-amino-4,5,7-trichloroisoindol-1-one; 3-amino-4,5,6,7-tetrachloroisoindol-1-one; 3-amino-4,5,7-trichloro-6-methylsulphanylisoindol-1-one; 3-amino-4,5,6,7-tetrabromoisoindol-1-one; 3-amino-4,5,6,7-tetrafluoroisoindol-1-one; 3-methylaminoisoindol-1-one; 3-ethylaminoisoindol-1-one; 3-propylaminoisoindol-1-one; 3-dimethylaminoisoindol-1-one; 7-ethylaminopyrrolo[3,4-b]pyrid-5-one; 7-aminopyrrolo[3,4-b]pyrid-5-one; 3-aminopyrrolo[3,4-c]pyrid-5-one; 3-amino-6-methylpyrrolo[3,4-c]pyrid-1-one; 5-aminopyrrolo[3,4-b]pyrid-7-one; 7-aminopyrrolo[3,4-b]pyrazin-5-one; 7-amino-2-methylpyrrolo[3,4-b]pyrazin-5-one; 7-amino-2,3-dimethylpyrrolo[3,4-b]pyrazin-5-one; 7-amino-2,3-dihydro-[1,4]dithiino[2,3-c]pyrrol-5-one; 3-imino-2-methyl-2,3-dihydroisoindol-1one; 3-imino-2-ethyl-2,3-dihydroisoindol-1-one; 3-imino-2-propyl-2,3-dihydroisoindol-1 -one; 2-hydroxymethyl-3-imino-2,3-dihydroisoindol-1-one; 2-(2-hydroxyethyl)-3-imino-2,3-dihydroisoindol-1-one; 2-(1-imino-3-oxo-1,3-dihydroisoindol-2-yl)ethanesulphonic acid; 3-(1-imino-3-oxo-1,3-dihydroisoindol-2-yl)propionic acid; 2-(3-hydroxypropyl)-3-imino-2,3-dihydroisoindol-1-one; and 5-imino-6-methyl-5,6-dihydropyrrolo[3,4-b]pyridin-7-one.

19. A process according to claim 8, wherein said salts are chosen from hydrochlorides; sulphates; hydrobromides; and tartrates.

20. A process according to claim 9, wherein said salts are chosen from hydrochlorides; sulphates; hydrobromides; and tartrates.

21. A process according to claim 11, wherein said salts are chosen from hydrochlorides; sulphates; hydrobromides; and tartrates.

22. A process according to claim 12, wherein said salts are chosen from hydrochlorides; sulphates; hydrobromides; and tartrates.

23. A process according to claim 1, wherein said at least one compound is chosen from 1,4-dimethylaminobenzaldehyde and 4-dimethylaminonaphthaldehyde.

24. A composition for dyeing at least one keratin fiber, wherein said composition comprises:

(a) at least one aliphatic cationic amine chosen from amines having formula (I) and the cosmetically acceptable salts thereof:

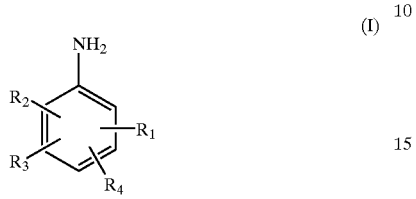

wherein:

R$_1$, R$_2$, R$_6$ and R$_4$, which may be identical or different, are each chosen from hydrogen, halogens; —NH$_2$ groups; —OH groups; —Z groups; —COZ groups; —COOZ groups; alkylcarbonyl groups; aminoalkylcarbonyl groups; N-alkylaminoalkylcarbonyl groups; N,N-dialkylaminoalkylcarbonyl groups; aminoalkylcarbonylalkyl groups; N-alkylaminoalkylcarbonylalkyl groups; N,N-dialkylaminoalkylcarbonylalkyl groups; carboxyl groups; alkylcarboxyl groups; alkylsulphonyl groups; aminosulphonyl groups; N-alkylaminosulphonyl groups; N,N-dialkylaminosulphonyl groups; aminosulphonylalkyl groups; N-alkylaminosulphonylalkyl groups; N,N-dialkylaminosulphonylalkyl groups; carbamyl groups; N-alkylcarbamyl groups; N,N-dialkylcarbamyl groups; carbamylalkyl groups; N-alkylcarbamylalkyl groups; N,N-dialkylcarbamylalkyl groups; alkyl groups; monohydroxyalkyl groups; polyhydroxyalkyl groups; alkoxyalkyl groups; trifluoroalkyl groups; cyano groups; —OR$_i$ groups; —SR$_i$ groups: —OR$_i$Z groups; —SR$_i$Z groups; and amino groups protected with at least one group chosen from alkylcarboxyl groups, trifluoroalkylcarbonyl groups, aminoalkylcarbonyl groups, carbonyl groups, N-alkylaminoalkylcarbonyl groups, N,N-dialkylaminoalkylcarbonyl groups, alkylcarboxyl groups, carbamyl groups, N-alkylcarbamyl groups, N,N-dialkylcarbamyl groups, alkylsulphonyl groups, aminosulphonyl groups, N-alkylaminosulphonyl groups, N,N-dialkylaminosulphonyl groups, thiocarbamyl groups, formyl groups, —COZ groups, and —COOZ groups;

wherein:

R$_i$, which may be identical or different, are each chosen from alkyl groups; monohydroxyalkyl groups; polyhydroxyalkyl groups; —Z groups; alkoxyalkyl groups; aryl groups; benzyl groups; carboxyalkyl groups; alkylcarboxyalkyl groups; cyanoalkyl groups; carbamylalkyl groups; N-alkylcarbamylalkyl groups; N,N-dialkylcarbamylalkyl groups; trifluoroalkyl groups; aminosulphonylalkyl groups; N-alkylaminosulphonylalkyl groups; N,N-dialkylaminosulphonylalkyl groups; alkylsulphinylalkyl groups; alkylsulphonylalkyl groups; alkylcarbonylalkyl groups; aminoalkyl groups; and aminoalkyl groups in which said amine is substituted with at least one group chosen from alkyl groups, monohydroxyalkyl groups, polyhydroxyalkyl groups, alkylcarbonyl groups, formyl groups, trifluoroalkylcarbonyl groups, alkylcarboxyl groups, carbamyl groups, N-alkylcarbamyl groups, N,N-dialkylcarbamyl groups, thiocarbamyl groups, alkylsulphonyl groups, —Z groups, —COZ groups, and —COOZ groups;

Z, which may be identical or different, are each chosen from groups having formula (II):

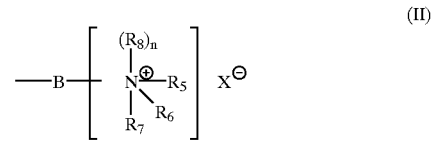

wherein:

B, which may be identical or different, are each chosen from linear divalent alkyl groups and branched divalent alkyl groups, optionally interrupted by at least one heteroatom, and optionally substituted with at least one group chosen from hydroxyl and C$_1$–C$_6$ alkoxy groups;

R$_5$, R$_6$ and R$_7$, which may be identical or different, are each chosen from alkyl groups; monohydroxyalkyl groups; polyhydroxyalkyl groups; alkoxyalkyl groups; cyanoalkyl groups; aryl groups; benzyl groups; carbamylalkyl groups; trialkylsilane alkyl groups; and aminoalkyl groups wherein said amine is protected with at least one group chosen from alkylcarbonyl groups, carbamyl groups, and alkylsulphonyl groups;

two of R$_5$, R$_6$ and R$_7$, may also form, together with the nitrogen atom to which they are attached, at least one ring, optionally substituted, chosen from 5-membered rings and 6-membered rings, wherein said at least one ring comprises at least one heteroatom; and at least one of R$_5$, R$_6$ and R$_7$, which may be identical or different, may also be chosen from —B' groups of a second —Z group, wherein said —B' groups are chosen from —B groups;

X$^\ominus$, which may be identical or different, are each chosen from monovalent anions and divalent anions;

R$_8$, which may be identical or different, are each chosen from alkyl groups; monohydroxyalkyl groups; polyhydroxyalkyl groups; aryl groups; benzyl groups; aminoalkyl groups; aminoalkyl groups wherein said amine is protected with at least one group chosen from alkylcarbonyl groups, carbamyl groups and alkylsulphonyl groups; carboxyalkyl groups; cyanoalkyl groups; carbamylalkyl groups; trifluoroalkyl groups; trialkylsilane alkyl groups; sulfonamidoalkyl groups; alkylcarboxyalkyl groups; alkylsulfinylalkyl groups; alkylsulfonylalkyl groups; alkylketoalkyl groups; N-alkylcarbamylalkyl groups; and N-alkylsulfonamidoalkyl groups;

n is an integer chosen from 0 and 1, with the proviso that, when n=0, B is attached to the nitrogen atom substituted with R$_5$, R$_6$ and R$_7$;

when n=1, two of R$_5$, R$_6$ and R$_7$ form, together with the nitrogen atom to which they are attached, at least one saturated ring, optionally substituted, chosen from 5-membered heterocycles and 6-membered heterocycles, wherein said at least one saturated ring one carbon atom of said at least one saturated ring; and with the proviso that that in said amine of formula (I), at least one of $R_1$, $R_2$, $R_3$, and $R_4$ comprises at least one Z group; and (b) at least one compound chosen from aldehydes; ketones; quinones; diiminoisoindoline derivatives; and 3-aminoisoindolone derivatives; with the proviso that said composition does not comprise an oxidizing agent.

25. A composition according to claim 24, wherein said at least one keratin fiber is a human keratin fiber.

26. A composition according to claim 25, wherein said human keratin fiber is hair.

27. A composition according to claim 24, further comprising at least one medium suitable for dyeing.

28. A composition according to claim 24, wherein said at least one heteroatom is chosen from oxygen; sulphur; and nitrogen.

29. A composition according to claim 24, wherein said monovalent and divalent anions are chosen from halogens; hydroxide anions; hydrogen sulphate anions; and alkyl sulphate anions.

30. A composition according to claim 24, wherein said halogens are chosen from chlorine; bromine; fluorine; and iodine.

31. A composition according to claim 24, wherein said alkyl sulphate anions are chosen from methyl sulphate and ethyl sulphate.

32. A composition according to claim 24, wherein said at least one compound is chosen from aldehydes having the formula (III) and the cosmetically acceptable salts thereof:

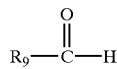
(III)

in which $R_9$ is chosen from groups having formula (III A):

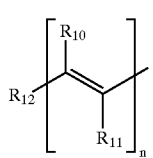
(III A)

in which:

$R_{10}$ and $R_{11}$, which may be identical or different, are each chosen from hydrogen; alkyl groups; monohydroxyalkyl groups; polyhydroxyalkyl groups; alkylhydroxyalkyl groups; alkoxy groups; —$CF_3$ groups; and —$OCF_3$ groups;

$R_{10}$ and $R_{11}$, which may be identical or different, may also form, together with the atoms to which they are attached, at least one ring, optionally substituted, chosen from aryl rings; 5-membered heterocyclic rings; and 6-membered heterocyclic rings;

n is an integer ranging from 0 to 3; and $R_{12}$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered heterocyclic groups, optionally substituted.

33. A composition according to claim 24, wherein said at least one compound is chosen from ketones having formula (IV), ketones having formula (V), and the cosmetically acceptable salts thereof:

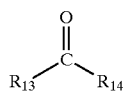
(IV)

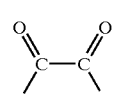
(V)

in which:

$R_{13}$ is chosen from groups having formula (III A):

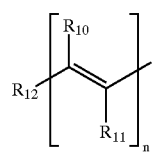
(III A)

in which:

$R_{10}$ and $R_{11}$, which may be identical or different, are each chosen from hydrogen; alkyl groups; monohydroxyalkyl groups; polyhydroxyalkyl groups; alkylhydroxyalkyl groups; alkoxy groups; —$CF_3$ groups; and —$OCF_3$ groups;

$R_{10}$ and $R_{11}$, which may be identical or different, may also form, together with the atoms to which they are attached, at least one ring, optionally substituted, chosen from aryl rings; 5-membered heterocyclic rings; and 6-membered heterocyclic rings;

n is an integer ranging from 0 to 3; and $R_{12}$ is chosen from hydrogen; alkyl groups; monohydroxyalkyl groups; polyhydroxyalkyl groups; alkylhydroxyalkyl groups; alkoxy groups; —$CF_3$ groups; —OCF, groups; aryl groups, optionally substituted; alkylaryl groups, optionally substituted; 5-membered heterocyclic groups, optionally substituted; and 6-membered heterocyclic groups, optionally substituted;

$R_{14}$ is chosen from alkyl groups; monohydroxyalkyl groups; polyhydroxyalkyl groups; alkylhydroxyalkyl groups; aryl groups, optionally substituted; alkylaryl groups, optionally substituted; 5-membered heterocyclic groups, optionally substituted; and 6-membered heterocyclic groups, optionally substituted;

$R_{13}$ and $R_{14}$ may also form, together with the atoms to which they are attached, at least one ring, optionally substituted, chosen from 5-membered aryl rings, 6-membered aryl rings, and heterocyclic rings, it being possible for said at least one ring itself to be attached to at least one ring, optionally substituted, chosen from 5-membered aryl rings, 6-membered aryl rings, and heterocyclic rings.

34. A composition according to claim 33, wherein said heterocyclic rings comprise at least one heteroatom chosen from N and S.

35. A composition according to claim 33, wherein said at least one compound is chosen from quinones having formula (VI), quinones having formula (VII), and the cosmetically acceptable salts thereof:

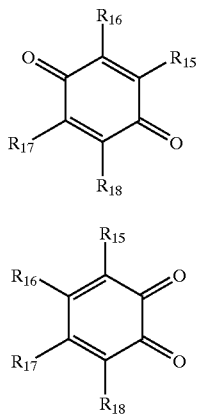

in which:
- $R_{15}$ is chosen from hydrogen; halogens; sulphonic groups; and alkoxy groups;
- $R_{16}$, $R_{17}$ and $R_{18}$, which may be identical or different, are each chosen from hydrogen; halogens; hydroxyl groups; alkyl groups; monohydroxyalkyl groups; polyhydroxyalkyl groups; alkylhydroxyalkyl groups; alkylsulphonyl groups; carboxyalkyl groups; aminoalkyl groups; alkylaminoalkyl groups; (dihydroxy)alkylaminoalkyl groups; alkyl-NR'R" groups, wherein R' and R", which may be identical or different, are each chosen from alkyl groups, or R' and R" may also form, together with the nitrogen atom to which they are attached, at least one ring chosen from aryl rings, 5-membered heterocycles and 6-membered heterocycles; aryl groups; amino groups, optionally substituted with at least one group chosen from alkyl groups and hydroxyalkyl groups; and
- at least one of $R_{15}$ and $R_{16}$, $R_{16}$ and $R_{17}$, and $R_{17}$ and $R_{18}$ may also form, together with the atoms to which they are attached, at least one ring, optionally substituted, chosen from aryl rings, 5-membered heterocycles, and 6-membered heterocycles.

36. A composition according to claim 24, wherein said at least one compound is chosen from diaminoisoindolines having formula (VII), 3-aminoisoindolone derivatives having formula (VII), and the cosmetically acceptable salts thereof:

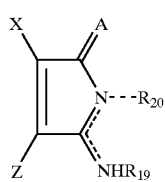

in which:
- $R_{19}$ and $R_{20}$, which may be identical or different, are each chosen from hydrogen; alkyl groups; monohydroxyalkyl groups; polyhydroxyalkyl groups; alkylhydroxyalkyl groups; aminoalkyl groups; alkylaminoalkyl groups; (dihydroxy)alkylaminoalkyl groups; and alkyl-NR'R" groups, wherein R' and R", which may be identical or different, are each chosen from alkyl groups, or R' and R" may also form, together with the nitrogen atom to which they are attached, at least one ring chosen from aryl rings, 5-membered heterocycles, and 6-membered heterocycles;
- A is chosen from oxygen and NH; and
- X and Z form, together with the atoms to which they are attached, at least one ring, optionally substituted, chosen from aryl rings, 5-membered heterocycles, and 6-membered heterocycles.

37. A composition according to claim 24, having a pH ranging from 2 to 11.

38. A composition according to claim 24, wherein said at least one aliphatic cationic amine is present in a concentration ranging from 0.01% to 10% by weight relative to the total weight of said composition.

39. A composition according to claim 38, wherein said at least one aliphatic cationic amine is present in a concentration ranging from 0.05% to 5% by weight relative to the total weight of said composition.

40. A composition according to claim 24, wherein said at least one compound is present in a concentration ranging from 0.01% to 10% by weight relative to the total weight of the composition.

41. A composition according to claim 40, wherein said at least one compound is present in a concentration ranging from 0.05% to 5% by weight relative to the total weight of the composition.

42. A composition according to claim 27, wherein said at least one medium suitable for dyeing is an aqueous medium chosen from water and organic solvents.

43. A composition according to claim 42, wherein said organic solvents are chosen from alcohols; glycols; glycol ethers; and mixtures thereof.

44. A composition according to claim 27, wherein said at least one medium is present in a concentration ranging from 0.5% to 20% by weight relative to the total weight of said composition.

45. A composition according to claim 24, further comprising at least one fatty amide.

46. A composition according to claim 45, wherein said at least one fatty amide is chosen from monoethanolamides of acids derived from copra; monoethanolamides of lauric acid; monoethanolamides of oleic acid; diethanolamides of acids derived from copra; diethanolamides of lauric acid; and diethanolamides of oleic acid.

47. A composition according to claim 45, wherein said at least one fatty amide is present in a concentration ranging from 0.05% to 10% by weight relative to the total weight of said composition.

48. A composition according to claim 24, further comprising at least one surfactant.

49. A composition according to claim 48, wherein said at least one surfactant is chosen from anionic surfactants; cationic surfactants; nonionic surfactants; amphoteric surfactants; and zwitterionic surfactants.

50. A composition according to claim 48, wherein said at least one surfactant is present in a concentration ranging from about 0.1% to about 50% by weight relative to the total weight of said composition.

51. A composition according to claim 50, wherein said at least one surfactant is present in a concentration ranging from about 1% to about 20% by weight relative to the total weight of said composition.

52. A composition according to claim 24, further comprising at least one thickener.

53. A composition according to claim 52, wherein said at least one thickener is present in a concentration ranging from about 0.2% to about 20% by weight relative to the total weight of said composition.

54. A composition according to claim 24, further comprising at least one cosmetically acceptable adjuvant chosen from antioxidants; fragrances; sequestering agents; dispersants; hair conditioners; preserving agents; and opacifiers.

55. A composition according to claim 24, wherein said composition is in the form of a liquid, a cream or a gel.

56. A composition according to claim 24, wherein said at least one aliphatic cationic amine is chosen from:
[2-(2,4-diaminophenoxy)ethyl]diethylmethylammonium chloride;
[3-(2,4-diaminophenoxy)propyl]triethylammonium chloride;
[2-(2,4-dihydroxyphenyl)-2-oxoethyl]triethylammonium chloride;
[2-(4-amino-2-hydroxyphenoxy)ethyl] diethylmethylammonium chloride;
triethyl[2-(3-hydroxy-4-methylphenylamino)ethyl] ammonium bromide;
triethyl[2-(3-hydroxy-2,4-dimethylphenyl-carbamoyloxy) ethyl]ammonium chloride;
[2-(4-chloro-5-hydroxyphenylamino)ethyl] triethylammonium bromide;
[2-(2,4-diaminophenoxy)ethyl]diethylmethylammonium chloride;
[2(2,4-diaminophenyl)ethyl]triethylammonium chloride;
triethyl[(3-hydroxy-4-methylphenylcarbamoyl) methylammonium chloride;
[2-[4-(dimethylamino)salicylamido]ethyl] diethylmethylammonium iodide;
ethyl(2-hydroxyethyl)dimethylammonium 4-(methylamino) salicylate bromide;
3-[(4-amino-2-hydroxybenzoyl)oxy]-N-ethyl-N,N-dimethyl-1-propylammonium iodide;
3-[(4-amino-2-hydroxybenzoyl)oxy]-N,N, N-trimethyl-1-propylammonium iodide;
triethyl(2-hydroxyethyl)ammonium 4-aminosalicylate bromide;
2-[(4-amino-2-hydroxybenzoyl)oxy]-N, N-diethyl-N-methylethylammonium iodide;
2-[(4-amino-2-hydroxybenzoyl)oxy]-N-ethyl-N, N-dimethylethylammonium iodide;
ethyl(2-hydroxyethyl)dimethylammonium 4-aminosalicylate bromide;
2-[(4-amino-2-hydroxybenzoyl)oxy]-N, N,N-trimethylethylammonium iodide;
{2-[2-aminophenylamino]ethyl}trimethylammonium monochloride monohydrate;
[2-(2-amino-5-chlorophenylamino)ethyl] trimethylammonium monochloride;
[2-(2-amino-6-chlorophenylamino)ethyl] trimethylammonium monochloride;
[2-(2-amino-4-chlorophenylamino)ethyl] trimethylammonium monochloride;
{2-[2-amino-4-chloro-5-(2-hydroxyethoxy)-phenylamino] ethyl}trimethylammonium monochloride;
[2-(2-amino-5-methoxyphenylamino)ethyl] trimethylammonium monochloride;
[2-(2-amino(2-hydroxyethyl)phenylamino)ethyl] dimethylammonium monobromide;
[3-(2-aminophenylamino)propyl]diethylmethylammonium monochloride;
[2-(2-amino-4-methylphenylamino)ethyl] trimethylammonium monochloride;
[2-(2,5-diaminophenoxy)ethyl]diethylmethylammonium chloride monohydrate;
N,N-bis(trimethylammoniumpropyl)-4-aminoaniline dichloride;
[4-(4-aminophenylamino)pentyl]diethylmethylammonium chloride;
[4-(4-aminophenylamino)pentyl]diethyl(2-hydroxyethyl) ammonium chloride;
[2-(4-aminophenylamino)ethyl]diethylmethylammonium chloride;
{2-[(4-aminophenyl)methylamino] ethyl}trimethylammonium chloride;
and the acid addition salts thereof.

57. A composition according to claim 24, wherein said at least one aliphatic cationic amine is chosen from:
[3-(4-aminophenylamino)propyl]trimethylammonium chloride;
[2-(4-aminophenylamino)propyl]trimethylammonium chloride;
[4-(4-amino-2-methylphenylamino)pentyl] diethylmethylammonium chloride;
[4-(4-amino-3-methylphenylamino)pentyl] diethylmethylammonium chloride;
N1, N4-bis[3-N-methyl-N-(4'-aminoaniline)ethyl]-1,1,4,4-tetramethyldiammonium 1,3-propane dibromide dihydrabromide monohydrate;
N1, N3-bis[3-N(4'-aminoaniline)propyl]-1,1,3,3-tetramethyldiammonium 1,3-propane dibromide monohydrate;
1,3-bis{[2-(4-aminoaniline)propyl]-1,1,3,3-tetramethyldiammoniumpropane dibromide;
1,3-bis{[4-(4-aminoaniline)pentyl]-1, 1,3,3-tetramethyldiammoniumpropane dichloride;
[4-(4-aminophenylamino)pentyl](5-amino-2-hydroxybenzyl)diethylammonium monochloride;
[2-(4-aminophenylamino)propyl](5-amino-2-hydroxybenzyl)dimethylammonium monochloride;
N1, N3-bis[3-N-(2'-aminoaniline)propyl]-1,1,3,3-tetramethyldiammonium 1,3-propane dibromide;
1,3-bis{[2-(2,4-diaminophenoxy)ethyl] diethylammonium}propane dibromide;
and the acid addition salts thereof.

58. A composition according to claim 24, wherein said at least one compound is chosen from benzaldehyde;
2-monohydroxybenzaldehyde;
3-monohydroxybenzaldehyde;
4-monohydroxybenzaldehyde;
2-monomethoxybenzaldehyde;
3-monomethoxybenzaldehyde;
4-monomethoxybenzaldehyde;
2-monomethylbenzaldehyde; 3-monomethylbenzaldehyde; 4-monomethylbenzaldehyde; (2,3)-dihydroxybenzaldehyde; (2,4)-dihydroxybenzaldehyde; (2,5)-dihydroxybenzaldehyde; (2,6)-dihydroxybenzaldehyde; (3,5)-dihydroxybenzaldehyde; (2,3)-dimethoxybenzaldehyde; (2,4)-dimethoxybenzaldehyde; (2,5)-dimethoxybenzaldehyde; (2,6)-dimethoxybenzaldehyde; (3,5)-dimethoxybenzaldehyde; vanillin; isovanillin; syringaldehyde; orthophthalaldehyde; isophthalaldehyde; terephthalaldehyde; (2,3)-dimethylbenzaldehyde; (2,4)-dimethylbenzaldehyde; (2,5)-dimethylbenzaldehyde; (2,6)-dimethylbenzaldehyde; (3,5)-dimethylbenzaldehyde; 4-isopropylbenzaldehyde; 4-dimethylaminobenzaldehyde; 4-diethylaminobenzaldehyde; piperonal; (2,6)-dimethyl-4-hydroxybenzaldehyde; (3,5)-dimethyl-4-hydroxybenzaldehyde; 2-mononitrobenzaldehyde; 3-mononitrobenzaldehyde; 4-mononitrobenzaldehyde; 2-hydroxy-3-methoxybenzaldehyde; 2-hydroxy-4-methoxybenzaldehyde; 2-hydroxy-5-methoxybenzaldehyde; 2-hydroxy-6- methoxybenzaldehyde; 4-methylthiobenzaldehyde; (2,3,4)-trihydroxybenzaldehyde; (2,4,6)-trihydroxybenzaldehyde; (3,4,5)-tri-hydroxybenzaldehyde; (2,4,5)-trihydroxybenzaldehyde; methyl 2-formyl benzoate; methyl 3-formyl benzoate; methyl 4-formyl benzoate; 2-mono(2-hydroxyethoxy)benzaldehyde; 3-mono(2-hydroxyethoxy)benzaldehyde; 4-mono(2-hydroxyethoxy)benzaldehyde; 4-nitro-3-hydroxybenzaldehyde; 3-nitro-4-hydroxybenzaldehyde; 2-nitro-4-hydroxybenzaldehyde; 3-nitro-2-hydroxybenzaldehyde; 2-monotrifluorobenzaldehyde; 3-monotrifluorobenzaldehyde; 4-monotrifluorobenzaldehyde; 2,3-dihydroxy-4-methoxybenzaldehyde; 3,4-dihydroxy-5-methoxybenzaldehyde; 3,5-dihydroxy-4-methoxybenzaldehyde; 3-methoxy-2-nitrobenzaldehyde; 4-methoxy-2-nitrobenzaldehyde; 2-methoxy-3-nitrobenzaldehyde; 4-methoxy-3-nitrobenzaldehyde; (2,3,4)-trimethoxybenzaldehyde; (2,4,6)-trimethoxybenzaldehyde; (3,4,5)-trimethoxybenzaldehyde; (2,4,5)-trimethoxybenzaldehyde; 5-nitrovanillin; (2,4)-dinitrobenzaldehyde; (2,6)-dinitrobenzaldehyde; pentamethylbenzaldehyde; 4-methylsulphonylbenzaldehyde; 2-monoformylphenoxyacetic acid; 3-monoformylphenoxyacetic acid; 4-monoformylphenoxyacetic acid; 4-diethylaminosalicylaldehyde; 4-(3-dimethylaminopropoxy)benzaldehyde; 2,3-dihydrobenzo-(b)furan-5-carboxaldehyde; 1-naphthaldehyde; 2-naphthaldehyde; 6-carboxaldehyde-1,4-benzodioxane; 5-carboxaldehyde-1,4-benzodioxane; 2-monohydroxy-1-naphthaldehyde; 4-monohydroxy-1-naphthaldehyde; 1-monohydroxy-2-naphthaldehyde; 1-(4-formylphenyl)imidazole; 4-pyrrolidinobenzaldehyde; 2-monomethoxy-1-naphthaldehyde; 4-monomethoxy-1-naphthaldehyde; 2,3-dimethylchroman-6-carboxaldehyde; 2,3,6,7-tetrahydro-1H,5H-pyrido(3,2,1-IJ)quinoline-9-carbaldehyde; 4-dimethylamino-1-naphthaldehyde; 9-anthraldehyde; 3-nitro-4-pyrrolidinobenzaldehyde; 3-nitro-4-piperidinobenzaldehyde; 3-nitro-4-morpholinobenzaldehyde; pyridine-2-monocarboxaldehyde; pyridine-3-monocarboxaldehyde; pyridine-4-monocarboxaldehyde; 2,6-pyridinodicarboxaldehyde; 5-formyl-6-methyluracil; pyridoxal; quinoline-2-monocarboxaldehyde; quinoline-3-monocarboxaldehyde; quinoline-4-monocarboxaldehyde; 8-hydroxyquinoline-2-carboxaldehyde; 2-furaldehyde; 3-furaldehyde; 2-thienylcarboxaldehyde; 3-thienylcarboxaldehyde; 2-imidazocarboxaldehyde; 3-imidazocarboxaldehyde; 2-pyrrolecarboxaldehyde; 5-nitro-2-furaldehyde; 5-(dimethylamino)-2-furaldehyde; 2,5-thiophenedicarboxaldehyde; 2,3-thiophenedicarboxaldehyde; pyrazole-3-carbaldehyde; 5-nitro-2-thiophenecarboxaldehyde; 5-nitro-3-thiophenecarboxaldehyde; indole-3-carboxaldehyde; N-methylindole-3-carboxaldehyde; 2-methylindole-3-carboxaldehyde; 4-monomethylindolecarboxaldehyde; 5-monomethylindolecarboxaldehyde; 6-monomethylindolecarboxaldehyde; 7-monomethylindolecarboxaldehyde; and 5-formyl-2-furansulphonic acid.

59. A composition according to claim 24, wherein said at least one compound is chosen from 2,3-indolinedione; 2,3-butanedione; 2,3-pentanedione; (2,3)-hexanedione; (3,4)-hexanedione; 1-phenyl-1,2-propanedione; benzil; furil; 2,2'-pyridil; nitrobenzil; anisil; 3,3'-dimethoxybenzil; 4,4'-bis(dimethylamino)benzil; camphoroquinone; cyclohexane-1,2-dione; isatin; N-methylisatin; 4-monomethylisatin; 5-monomethylisatin; 6-monomethylisatin; 7-monomethylisatin; (4,5)-dimethylisatin; (4,7)-dimethylisatin; (5,7)-dimethylisatin; (6,7)-dimethylisatin; N-ethylisatin; N-hydroxymethylisatin; 5-monomethoxyisatin; 6-monomethoxyisatin; 7-monomethoxyisatin; 4-monochloroisatin; 5-monochloroisatin; 6-monochloroisatin; 7-monochloroisatin; 4-monobromoisatin; 5-monobromoisatin; 6-monobromoisatin; 7-monobromoisatin; N-isopropylisatin; N-butylisatin; N-propylisatin; 5-nitroisatin; isatin-5-sulphonic acid; 2,4,5-trihydroxypyrimidine; alloxan; 1,3-dimethylhexahydro-2,4,5,6-pyrimidinetetraone; ninhydrin; chinisatin; 1,3-indenedione; squaric acid; croconic acid; 3,4-dimethoxy-3-cyclobutene-1,2-dione; 3-ethoxy-3-cyclobutene-1,2-dione; 4-ethoxy-3-cyclobutene-1,2-dione; 3-isopropoxy-3-cyclobutene-1,2-dione; 4-isopropoxy-3-cyclobutene-1,2-dione; 3,4-di-N-butoxy-3-cyclobutene-1,2-dione; rhodizonic acid; oxindole; N-methyl-2-indolinone; N-methylnitro-2-indolinone; 6-methoxyoxindole; 5,6-dimethoxy-oxindole; 5-monochlorooxindole; and 6-monochlorooxindole.

60. A composition according to claim 24, wherein said at least one compound is chosen from 1,4-naphthoquinone; spinulosin; atromentin; aurentioglyocladin; 2,5-dihydroxy-6-methylbenzoquinone; 2-hydroxy-3-methyl-6-methoxybenzoquinone; 2,5-dihydroxy-3,6-diphenylbenzoquinone; 2,3-dimethyl-5-hydroxy-6-methoxybenzoquinone; 2,5-dihydroxy-6-isopropylbenzoquinone; lawsone; juglone; fafioline; naphthazarine; naphthopurpurine; lapachol; plumbagin; chloroplumbagin; droserone; shikonine; 2-hydroxy-3-methyl-1,4-naphthoquinone; 3,5-dihydroxy-1,4-naphthoquinone; 2,5-dihydroxy-1,4-naphthoquinone; 2-methoxy-5-hydroxy-1,4-naphthoquinone; 3-methoxy-5-hydroxy-1,4-naphthoquinone; (1,4)-naphthoquinone; (1,2)-naphthoquinone; 4,5-dimethoxy-1,2-benzoquinone; phenanthrenequinone; and (1,2)-naphthoquinone-4-sulphonic acid.

61. A composition according to claim 24, wherein said at least one compound is chosen from 3-imino-3H-isoindolylamine; 3-imino-4-methyl-3H-isoindol-1-ylamine; 3-imino-4-tert-butyl-3H-isoindol-1-ylamine; 3-imino-7-nitro-3H-isoindol-1-ylamine; 3-amino-1-imino-1H-isoindol-4-ol; 3-imino-7-isopropoxy-3H-isoindol-1-ylamine; 3-imino-7-(2,2,2-trifluoroethoxy)-3H-isoindol-1-ylamine; 3-imino-7-ethoxy-3H-isoindol-1-ylamine; 3-imino-7-butoxy-3H-isoindol-1-ylamine; 3-amino-1-imino-1H-isoindole-4-sulphonic acid; 3-imino-7-chloro-3H-isoindol-1-ylamine; 3-imino-5-methyl-3H-isoindol-1-ylamine; 3-imino-5-ethyl-3H-isoindol-1-ylamine; 3-imino-5-tert-butyl-3H-isoindol-1-ylamine; 3-imino-5-amino-3H-isoindol-1-ylamine; N-(1-amino-3-imino-3H-isoindol-5-yl)acetamide; 3-imino-5-nitro-3H-isoindol-1-ylamine; 3-imino-5-fluoro-3H-isoindol-1-ylamine; 3-imino-5-chloro-3H-isoindol-1-ylamine; 3-imino-5-methylsulfonyl-3H-isoindol-1-ylamine; 3-imino-5-methoxy-3H-isoindol-1-ylamine; 3-imino-5-ethoxy-3H-isoindol-1-ylamine; 3-imino-5-propoxy-3H-isoindol-1-ylamine; 3-imino-5-isopropoxy-3H-isoindol-1-yl-amine; 3-imino-5-butoxy-3H-isoindol-1-ylamine; 3-imino-5-isobutoxy-3H-isoindol-1-ylamine; 3-imino-5-tert-butoxy-3H-isoindol-1-ylamine; 3-imino-5-(2,2,2-trifluoromethyl)-3H-isoindol-1-ylamine; 3-imino-5-(2,2,2-trifluoroethoxy)-3H-isoindol-1-ylamine; 3-imino-5-methanesulphonyl-3H-isoindol-1-ylamine; 3-imino-5,6-dimethyl-3H-isoindol-1-ylamine; 3-imino-5,6- diethyl-3H-isoindol-1-ylamine; 3-imino-5,6-dimethoxy-3H-isoindol-1-ylamine; 3-imino-5,6-diethoxy-3H-isoindol-1-ylamine; 3-imino-5,6-dibutoxy-3H-isoindol-1-ylamine; 3-imino-5,6-bis(trifluoromethyl)-3H-isoindol-1-ylamine; 3-imino-5,6-dichloro-3H-isoindol-1-ylamine; 5,6-bis (ethoxymethyl)3-imino-3H-isoindol-1-ylamine; 3-amino-1-imino-1H-isoindole-4,7-diol; 4,7-dichloro-3-imino-3H-isoindol-1-ylamine; 4,5,7-trichloro-3-imino-N6,N6-dimethyl-3H-isoindole-1,6-diamine; 4,5,6,7-tetrachloro-3-imino-3H-isoindol-1-ylamine; 4,5,6,7-tetrafluoro-3-imino-3H-isoindol-1-ylamine; 3-butylimino-3H-isoindol-1-ylamine; 2-(3-aminoisoindol-1-ylideneamino)ethanol; 3-(3-aminoisoindol-1-ylideneamino)-3-methylpentane-1,5-diol; N-(3-aminoisoindol-1-ylidene)guanidine; 7H-pyrrolo[3,4-b]pyrid-5-ylamine; 7-imino-7H-pyrrolo[3,4-b]pyrazin-5-ylamine; 7-imino-2,3-dimethyl-7H-pyrrolo[3,4-b]pyrazin-5-ylamine; 7-imino-7H-[1,4]dithiino[2,3-c]pyrrol-5-ylamine; 7-imino-2,3-dimethy-7H-[1,4]dithiino[2,3-c]pyrrol-5-ylamine; 7-imino-2,3-dihydro-7H-[1,4]dithiino[23-c]pyrrol-5-ylamine; 7-imino-2-methyl-2,3-dihydro-7H-[1,4]dithiino[2,3-c]pyrrol-5-ylamine; 3-aminoisoindol-1-one; 3-amino-7-methylisoindol-1-one; 3-amino-7-hydroxymethylisoindol-1-one; 3-amino-7-chloroisoindol-1-one; 3-amino-4-chloroisoindol-1-one; 3-amino-1-oxo-1H-isoindole-4-sulphonic acid; 3-amino-4-nitroisoindol-1-one; 3-amino-6-nitroisoindol-1-one; 3-amino-6-methylisoindol-1-one; 3-amino-6-chloro-isoindol-1-one; 3-amino-6-bromo-isoindol-1-one; 3-amino-6-methylsulphanylisoindol-1-one; 3-amino-6-methoxyisoindol-1-one; 3-amino-5-chloroisoindol-1-one; 3-amino-5-fluoroisoindol-1-one; 3-amino-5-methoxyisoindol-1-one; 3-amino-5-nitroisoindol-1-one; ethyl 3-amino-1-oxo-1H-isoindole-5-carboxylate; 3-amino-5,6-dichloroisoindol-1-one; 3-amino-5,6-di-bromoisoindol-1-one; 3-amino-4,7-dichloroisoindol-1-one; 3-amino-4,5,7-trichloroisoindol-1-one; 3-amino-4,5,6,7-tetrachloroisoindol-1-one; 3-amino-4,5,7-trichloro-6-methylsulphanylisoindol-1-one; 3-amino-4,5,6,7-tetrabromoisoindol-1-one; 3-amino-4,5,6,7-tetrafluoroisoindol-1-one; 3-methylaminoisoindol-1-one; 3-ethylaminoisoindol-1-one; 3-propylaminoisoindol-1-one; 3-dimethylaminoisoindol-1-one; 7-ethylaminopyrrolo[3,4-b]pyrid-5-one; 7-aminopyrrolo[3,4-b]pyrid-5-one; 3-aminopyrrolo[3,4-c]pyrid-5-one; 3-amino-6-methylpyrrolo[3,4-c]pyrid-1-one; 5-aminopyrrolo[3,4-b]pyrid-7-one; 7-aminopyrrolo[3,4-b]pyrazin-5-one; 7-amino-2-methylpyrrolo[3,4-b]pyrazin-5-one; 7-amino-2,3-d imethylpyrrolo[3,4-b]pyrazin-5-one; 7-amino-2,3-dihydro-[1,4]dithiino[2,3-c]pyrrol-5-one; 3-imino-2-methyl-2,3-dihydroisoindol-1-one; 3-imino-2-ethyl-2,3-dihydroisoindol-1-one; 3-imino-2-propyl-2,3-dihydroisoindol-1-one; 2-hydroxymethyl-3-imino-2,3-dihydroisoindol-1-one; 2-(2-hydroxyethyl)-3-imino-2,3-dihydroisoindol-1-one; 2-(1-imino-3-oxo-1,3-dihydroisoindol-2-yl)ethanesulphonic acid; 3-(1-imino-3-oxo-1,3-dihydroisoindol-2-yl)propionic acid; 2-(3-hydroxypropyl)-3-imino-2,3-dihydroisoindol-1-one; and 5-imino-6-methyl-5,6-dihydropyrrolo[3,4-b]pyridin-7-one.

62. A composition according to claim 32, wherein said salts are chosen 7from hydrochlorides; sulphates; hydrobromides; and tartrates.

63. A composition according to claim 33, wherein said salts are chosen from hydrochlorides; sulphates; hydrobromides; and tartrates.

64. A composition according to claim 35, wherein said salts are chosen from hydrochlorides; sulphates; hydrobromides; and tartrates.

65. A composition according to claim 36, wherein said salts are chosen from hydrochlorides; sulphates; hydrobromides; and tartrates.

66. A composition according to claim 24, wherein said at least one compound is chosen from 1,4-dimethylaminobenzaldehyde and 4-dimethylaminonaphthaldehyde.

67. A multi-compartment device or dyeing kit, wherein said device or dyeing kit comprises at least two compartments, wherein:

(a) a first compartment comprises a component (A); and (b) a second compartment comprises a component (B);

wherein said component (A) comprises a composition comprising at least one aliphatic cationic amine chosen from amines having formula (I) and the cosmetically acceptable salts thereof:

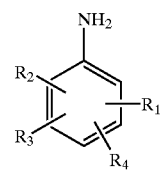

(I)

wherein:

$R_1$, $R_2$, $R_3$ and $R_4$, which may be identical or different, are each chosen from hydrogen; halogens; —$NH_2$ groups; —OH groups; —Z groups; —COZ groups; —COOZ groups; alkylcarbonyl groups; aminoalkylcarbonyl groups; N-alkylaminoalkylcarbonyl groups; N,N-dialkylaminoalkylcarbonyl groups; aminoalkylcarbonylalkyl groups; N-alkylaminoalkylcarbonylalkyl groups; N,N-dialkylaminoalkylcarbonylalkyl groups; carboxyl groups, alkylcarboxyl groups; alkylsulphonyl groups; aminosulphonyl groups; N-alkylaminosulphonyl groups; N,N-dialkylaminosulphonyl groups; aminosulphonylalkyl groups; N-alkylaminosulphonylalkyl groups; N,N-dialkylaminosulphonylalkyl groups; carbamyl groups; N-alkylcarbamyl groups; N,N-dialkylcarbamyl groups; carbamylalkyl groups; N-alkylcarbamylalkyl groups; N,N-dialkylcarbamylalkyl groups; alkyl groups; monohydroxyalkyl groups; polyhydroxyalkyl groups; alkoxyalkyl groups; trifluoroalkyi groups; cyano groups; —$OR_1$ groups; —$SR_1$ groups; —$OR_1Z$ groups; —$SR_1Z$ groups; and amino groups protected with at least one group chosen from alkylcarboxyl groups, trifluoroalkylcarbonyl groups, aminoalkylcarbonyl groups, carbonyl groups, N-alkylaminoalkylcarbonyl groups, N, N-dialkylaminoalkylcarbonyl groups, alkylcarboxyl groups, carbamyl groups, N,alkylcarbamyl groups, N,N-dialkylcarbamyl groups, alkylsulphonyl groups, aminosulphonyl groups, N-alkylaminosulphonyl groups, N,N-dialkylaminosulphonyl groups, thiocarbamyl groups, formyl groups, —COZ groups, and —COOZ groups;

wherein:

$R_1$, which may be identical or different, are each chosen from alkyl groups; monohydroxyalkyl groups; polyhydroxyalkyl groups; —Z groups; alkoxyalkyl groups; aryl groups; benzyl groups; carboxyalkyl groups; alkylcarboxyalkyl groups; cyanoalkyl groups; carbamylalkyl groups; N-alkylcarbamylalkyl groups; N,N-dialkylcarbamylalkyl groups; trifluoroalkyl groups; aminosulphonylalkyl groups; N-alkylaminosulphonylalkyl groups; N,N-dialkylaminosulphonylalkyl groups; alkylsulphinylalkyl groups; alkylsulphonylalkyl groups; alkylcarbonylalkyl groups; aminoalkyl groups; and aminoalkyl groups in which said amine is substituted with at least one group chosen from alkyl groups, monohydroxyalkyl groups, polyhydroxyalkyl groups, alkylcarbonyl groups, formyl groups, trifluoroalkylcarbonyl groups, alkylcarboxyl groups, carbamyl groups, N-alkylcarbamyl groups, N,N-dialkylcarbamyl groups, thiocarbamyl groups, alkylsulphonyl groups, —Z groups, —COZ groups, and —COOZ groups;

Z, which may be identical or different, are each chosen from groups having formula (II):

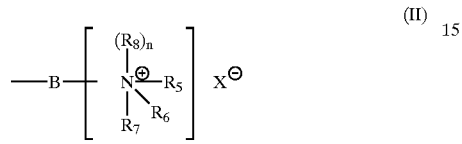
(II)

wherein:

B, which may be identical or different, are each chosen from linear divalent alkyl groups and branched divalent alkyl groups, optionally interrupted by at least one heteroatom, and optionally substituted with at least one group chosen from hydroxyl and $C_1$–$C_6$ alkoxy groups;

$R_5$, $R_6$ and $R_7$, which may be identical or different, are each chosen from alkyl groups; monohydroxyalkyl groups; polyhydroxyalkyl groups; alkoxyalkyl groups; cyanoalkyl groups; aryl groups; benzyl groups; carbamylalkyl groups; trialkylsilane alkyl groups; and aminoalkyl groups wherein said amine is protected with at least one group chosen from alkylcarbonyl groups, carbamyl groups, and alkylsulphonyl groups;

two of $R_5$, $R_6$ and $R_7$, may also form, together with the nitrogen atom to which they are attached, at least one ring, optionally substituted, chosen from 5-membered rings and 6-membered rings, wherein said at least one ring comprises at least one heteroatom; and at least one of $R_5$, $R_6$ and $R_7$, which may be identical or different, may also be chosen from —B' groups of a second —Z group, wherein said —B' groups are chosen from —B groups;

$X^\ominus$, which may be identical or different, are each chosen from monovalent anions and divalent anions;

$R_8$, which may be identical or different, are each chosen from alkyl groups; monohydroxyalkyl groups; polyhydroxyalkyl groups; aryl groups; benzyl groups; aminoalkyl groups; aminoalkyl groups wherein said amine is protected with at least one group chosen from alkylcarbonyl groups, carbamyl groups and alkylsulphonyl groups; carboxyalkyl groups; cyanoalkyl groups; carbamylalkyl groups; trifluoroalkyl groups; trialkylsilane alkyl groups; sulfonamidoalkyl groups; alkylcarboxyalkyl groups; alkylsulfinylalkyl groups; alkylsulfonylalkyl groups; alkylketoalkyl groups; N-alkylcarbamylalkyl groups; and N-alkylsulfonamidoalkyl groups;

n is an integer chosen from 0 and 1,
with the proviso that,
when n=0, B is attached to the nitrogen atom substituted with $R_5$, $R_6$ and $R_7$;
when n=1, two of $R_5$, $R_6$ and $R_7$ form, together with the nitrogen atom to which they are attached, at least one saturated ring, optionally substituted, chosen from 5-membered heterocycles and 6-membered heterocycles, wherein said at least one saturated ring comprises at least one heteroatom, and B is attached to at least one carbon atom of said at least one saturated ring, and with the proviso that in said amine of formula (I), at least one of $R_1$, $R_2$, $R_3$, and $R_4$ comprises at least one Z group; and wherein said component (B) comprises a composition comprising at least one compound chosen from aldehydes; ketones; quinones; diiminoisoindoline derivatives: and 3-aminoisoindolone derivatives; and further wherein said device or dyeing kit does not comprise an oxidizing agent.

68. A multi-compartment device or dyeing kit according to claim 67, wherein at least one component chosen from said component (A) and said component (B) is in the form of an anhydrous composition; and wherein said device or dyeing kit comprises a third compartment comprising a cosmetically acceptable aqueous medium which is suitable for dyeing and which is intended to be mixed, before use, into at least one compartment chosen from said first compartment comprising said component (A) and said second compartment said component (B).

* * * * *

UNITED STATES PATENT AND TRADEMARK OFFICE
CERTIFICATE OF CORRECTION

PATENT NO. : 6,458,168 B1
DATED : October 1, 2002
INVENTOR(S) : Alain Lagrange et al.

It is certified that error appears in the above-identified patent and that said Letters Patent is hereby corrected as shown below:

Title Page, Item [54] and Column 1, lines 5-6,
"3-AMINOISOINDOLONE" should read -- 3-AMINO-ISOINDOLONE --.

Column 15,
Line 67, "formula (II)." should read -- formula (II): --.

Column 16,
Line 32, "second 'Z group," should read -- second -Z group, --.

Column 21,
Lines 18-19, "N1, N4-bis[3-N-methyl-N-(4'-aminoaniline)ethyl]-1,1,4,4-tetramethyldiammonium" should read -- N1,N4-bis[3-N-methy1-N-(4'-aminoaniline) ethyl]-1,1,4,4-tetramethyldiammonium --.
Line 20, before "monohydrate;", delete "propane dibromide".
Lines 21-22, "N1, N3-bis[3-N(4'-aminoaniline)propyl]-1,1,3,3-tetramethyldiammonium" should read -- "N1,N3-bis[3-N(4'-aminoaniline)propyl]-1,1,3,3-tetramethyldiammonium --.
Lines 32-33, "N1, N3-bis[3-N-(2'-aminoaniline)propyl]-1,1,3,3-tetramethyldiammonium" should read -- N1,N3-bis[3-N-(2'-aminoaniline)propyl]-1,1,3,3-tetramethyldiammonium --.

Column 22,
Lines 26-27, "2,3dihydrobenzo(b)furan-5-carboxaldehyde;" should read
-- 2,3-dihydrobenzo(b)furan-5-carboxaldehyde; --.
Line 55, "4 -monomethylindolecarboxaldehyde;" should read
-- 4-monomethylindolecarboxaldehyde; --.

Column 23,
Line 19, "6methoxyoxindole;" should read -- 6-methoxyoxindole; --.
Line 47, "3-amino-l-imino-1 H-isoindole-4-sulphonic" should read
-- 3-amino-l-imino-lH-isoindole-4-sulphonic --.
Lines 49-50, "3-imino-5-ethyl-3H-isoindol-1 -ylamine;" should read
-- 3-imino-5-ethyl-3H-isoindol-1-ylamine; --.

Column 24,
Lines 15-16, "7-imino-2,3-dimethyl- 7H-[1,4]dithiino[2,3-c]pyrrol-5-ylamine;" should read -- 7-imino-2,3-dimethyl-7H-[1,4]dithiino[2,3-c]pyrrol-5-ylamine; --.
Lines 16-17, "7-imino-2,3-dihydro-7H-[1,4]dithiino[2,3 -c]pyrrol-5-ylamine;" should read -- 7-imino,-2,3-dihydro-7H-[1,4]dithiino[2,3-c]pyrrol-5-ylamine; --.
Lines 46-47, "3-imino-2-methyl-2,3-dihydroisoindol-lone;" should read
-- 3-imino-2-methyl-2,3-dihydroisoindol-l-one; --.
Lines 48-49, "3-imino-2-propyl-2,3-dihydroisoindol-1 -one;" should read
-- 3-imino-2-propyl-2,3-dihydroisoindol-l-one; --.

UNITED STATES PATENT AND TRADEMARK OFFICE
CERTIFICATE OF CORRECTION

PATENT NO. : 6,458,168 B1
DATED : October 1, 2002
INVENTOR(S) : Alain Lagrange et al.

It is certified that error appears in the above-identified patent and that said Letters Patent is hereby corrected as shown below:

Column 25,
Line 20, "$R_6$" should read -- $R_3$ --.
Line 21, "hydrogen," should read -- hydrogen; --.
Line 39, "-$SR_i$ groups:" should read -- -$SR_i$ groups;--.
Line 61, "groups:" should read -- groups; --.

Column 26,
Line 66, after "one saturated ring", insert -- comprises at least one heteroatom, and B is attached to at least --.

Column 28,
Line 41, "-OCF, groups;" should read -- $OCF_3$ groups; --.

Column 29,
Line 45, "formula (VII)," should read -- formula (VIII), --.
Line 46, "formula (VII)," should read -- formula (VIII), --.

Column 31,
Lines 34-35, "3-[(4-amino-2-hydroxybenzoyl)oxy]-N,N, N-trimethyl-l-propylammonium" should read -- 3-[(4-amino-2-hydroxybenzoyl)oxy]-N,N,N-trimethyl-l- propylammonium --.
Lines 38-39, "-2-[(4-amino-2-hydroxybenzoyl)oxy]-N, N-diethyl-N-methylethylammo-nium" should read -- 2-[(4-amino-2-hydroxybenzoyl)oxy]-N,N-diethyl-N-methylethylammonium --.
Lines 44-45, "2-[(4-amino-2-hydroxybenzoyl)oxy]-N, N,N-trimethylethylammonium" should read -- 2-[(4-amino-2-hydroxybenzoyl)oxy]-N,N,N-trimethylethylammonium --.

Column 32
Lines 20-21, "N1, N4-bis[3-N-methyl-N-(4'-aminoaniline)ethyl]-1,1,4,4-tetramethyldiammonium" should read -- N1,N4-bis [3-N-methyl-N-(4'-aminoaniline)ethyl]-1,1,4,4- tetramethyldiammonium --.
Lines 23-24, "Nl, N3-bis[3-N(4'-aminoaniline)propyl]-1,1,3,3-tetramethyldiammonium" should read -- Nl,N3-bis[3-N(4'-aminoaniline)propyl]-1,1,3,3-tetramethyldiammonium --.
Lines 28-29, "1,3-bis{[4-(4-aminoaniline)pentyl]-1, 1,3,3-tetramethyldiammoniumpropane" should read -- 1,3-bis {[4-(4-aminoaniline)pentyl]-1,1,3,3-tetramethyldiammoniumpropane --.
Lines 34-35, "N1, N3-bis[3-N-(2'-aminoaniline)propyl]-1,1,3,3-tetramethyldiammonium" should read -- N1,N3-bis[3-N-(2'-aminoaniline)propyl]-1,1,3,3-tetramethyldiammonium --.

UNITED STATES PATENT AND TRADEMARK OFFICE
CERTIFICATE OF CORRECTION

PATENT NO. : 6,458,168 B1
DATED : October 1, 2002
INVENTOR(S) : Alain Lagrange et al.

It is certified that error appears in the above-identified patent and that said Letters Patent is hereby corrected as shown below:

Column 33,
Lines 36-37, "2,3,6,7-tetrahydro-1 H,5H-pyrido(3,2,1-IJ)quinoline-9-carbaldehyde;" should read -- 2,3,6,7-tetrahydro-1H,5H-pyrido(3,2,1-IJ)quinoline-9-carbaldehyde; --.

Column 34,
Line 48, "3 -imino-7-ethoxy-3H-isoindol-1-ylamine;" should read -- 3-imino-7-ethoxy-3 H-isoindol-1-ylamine; --.
Lines 57-58, "3-imino-5-methylsulfonyl-3H-isoindol-1-ylamine;" should read -- 3-imino-5-methylsulphanyl-3H-isoindol-1-ylamine; --.
Lines 60-61, "3-imino-5-isopropoxy-3H-isoindol-l-yl-amine;" should read -- 3-imino-5-isopropoxy-3H-isoindol-1-ylamine; --.

Column 35,
Line 13, "N-(3 -aminoisoindol-1-ylidene)guanidine;" should read -- N-(3-aminoisoindol-1-ylidene)guanidine; --.
Lines 13-14, "7H-pyrrolo[3,4-b]pyrid-5-ylamine;" should read -- 7-imino-7H-pyrrolo[3,4-b]pyrid-5-ylamine; --.
Lines, 17-18, "7-imino-2,3-dimethy-7H-[1,4]dithiino[2,3-c]pyrrol-5-ylamine;" should read -- 7-imino-2,3-dimethyl-7H-[1,4]dithiino [2,3-c]pyrrol-5-ylamine; --.
Lines 18-19, "7-imino-2,3-dihydro-7H-[1,4]dithiino[23-c]pyrrol-5-ylamine;" should read -- 7-imino-2,3-dihydro-7H-[ 1,4]dithiino[2,3-c]pyrrol-5-ylamine; --.
Lines 44-45, "7-amino-2,3-d imethylpyrrolo[3,4-b]pyrazin-5-one;" should read -- 7-amino-2,3-dimethylpyrrolo[3,4-b]pyrazin-5-one; --.
Line 57, "chosen 7from" should read -- chosen from --.

Column 36,
Line 43, "trifluoroalkyi" should read -- trifluoroalkyl --.
Line 44, "-$OR_l$ groups; -$SR_1$ groups; -$OR_1Z$ groups;" should read -- -$OR_i$ groups; -$SR_i$ groups; -$OR_iZ$ groups; --.
Line 45, "-$SR_1Z$ groups;" should read -- -$SR_iZ$ groups; --.
Line 50, "N,alkylcarbamyl" should read -- N-alkylcarbamyl --.
Line 57, "$R_l$," should read -- $R_1$, --.

UNITED STATES PATENT AND TRADEMARK OFFICE
CERTIFICATE OF CORRECTION

PATENT NO. : 6,458,168 B1
DATED : October 1, 2002
INVENTOR(S) : Alain Lagrange et al.

It is certified that error appears in the above-identified patent and that said Letters Patent is hereby corrected as shown below:

<u>Column 38,</u>
Line 25, "ring," should read -- ring; --.
Line 32, "derivatives:" should read -- derivatives; --.
Line 45, before "said component (B).", insert -- comprising --.

Signed and Sealed this

Twenty-seventh Day of May, 2003

JAMES E. ROGAN
*Director of the United States Patent and Trademark Office*